(12) United States Patent
Kato

(10) Patent No.: US 8,211,039 B2
(45) Date of Patent: Jul. 3, 2012

(54) MEDICAL GUIDE WIRE, A METHOD OF MAKING THE SAME, AN ASSEMBLY OF BALLOON CATHETER AND GUIDING CATHETER COMBINED WITH THE MEDICAL GUIDE WIRE, AN ASSEMBLY OF MICROCATHETER AND GUIDING CATHETER COMBINED WITH THE MEDICAL GUIDE WIRE

(75) Inventor: Tomihisa Kato, Aichi (JP)

(73) Assignee: PatentStra Co., Ltd., Aichi (JP)

( * ) Notice: Subject to any disclaimer, the term of this patent is extended or adjusted under 35 U.S.C. 154(b) by 37 days.

(21) Appl. No.: 12/883,461

(22) Filed: Sep. 16, 2010

(65) Prior Publication Data

US 2011/0066106 A1    Mar. 17, 2011

(51) Int. Cl.
*A61M 25/00* (2006.01)
(52) U.S. Cl. ....................................................... 600/585
(58) Field of Classification Search ................... 600/433, 600/434, 585; 606/164.13
See application file for complete search history.

(56) References Cited

U.S. PATENT DOCUMENTS

| | | |
|---|---|---|
| 2005/0022572 A1 | 2/2005 | Kato et al. |
| 2008/0171217 A1 | 7/2008 | Mishima .................. 428/586 |

FOREIGN PATENT DOCUMENTS

| | | |
|---|---|---|
| EP | 2 269 684 A1 | 1/2011 |
| JP | 2000-512691 | 9/2000 |
| JP | 2003-342696 | 12/2003 |
| JP | 2005-014040 | 1/2005 |
| JP | 2007-330288 | 12/2007 |
| WO | WO 98/46804 | 10/1998 |

*Primary Examiner* — Max Hindenburg
*Assistant Examiner* — Jonathan M Foreman
(74) *Attorney, Agent, or Firm* — Morgan, Lewis & Bockius LLP

(57) ABSTRACT

In a medical guide wire 1, a flexible core wire 2 is made of austenitic stainless steel wire treated with a solid solution procedure, and drawn with a whole cross sectional reduction ratio as 90%-97.6%. Each time when the core wire 2 is subjected to a series of mechanical procedures, the core wire 2 is heat treated repetitively at low temperature subsequent to the mechanical procedures to improve a tensile strength characteristic of the core wire 2. The core wire 2 is twisted under the low heat treatment. Effectively used is a heat generated from a synthetic layer 6 when coating the layer 6 on the helical spring body 3. This makes it possible to increase the characteristic of the tensile strength of the core wire 2 with its thermal conductivity taken into consideration. Upon improving the tensile strength of the core wire 2, optimal conditions are achieved by observing a relationship between the tensile strength and the temperature which the core wire 2 exhibits when tightly drawn as a wrought-out procedure.

11 Claims, 11 Drawing Sheets side elevational view side elevational view

MEDICAL GUIDE WIRE, A METHOD OF MAKING THE SAME, AN ASSEMBLY OF BALLOON CATHETER AND GUIDING CATHETER COMBINED WITH THE MEDICAL GUIDE WIRE, AN ASSEMBLY OF MICROCATHETER AND GUIDING CATHETER COMBINED WITH THE MEDICAL GUIDE WIRE

BACKGROUND OF THE INVENTION

1. Field of the Invention

The present invention relates to medical guide wire and a method of making the same in which a stainless steel wire is subjected to a series of mechanical procedures, and thereafter heat treated at low temperature within a predetermined temperature range in order to improve a mechanical strength characteristic of the core wire.

2. Description of Related Art

In general, a medical guide wire (referred to simply as a guide wire) is thinned so that the guide wire is inserted into a somatic vasculature. With the thinned wire in mind, it is necessary to impart mechanical requirements to the guide wire with safety measures secured for a human body. For this purpose, various types of contrivances have been introduced.

In Japanese Laid-open Patent Application No. 2003-342696 (referred to as first reference), the first reference discloses mechanical procedures and heat treatment in low temperature with the use of a high silicic stainless steel (Si: 3.0%-5.0% by weight) as a core wire. The first reference uses various heat treatments for the purpose of providing the core wire with a high tensile strength.

In Japanese Patent Application Publication No. 2000-512691 (referred to as second reference), the second reference uses an elastic shape-memory alloy to improve a product quality by undergoing certain types of mechanical procedure.

In Japanese Laid-open Patent Application No. 2005-14040 (referred to as third reference), the third reference discloses a thinned wire which is divided into several regions, each of which is twisted and heat treated in varying degrees for the purpose of improving a product quality.

With the above three references in mind, an austenitic stainless steel wire is used as a material of the core wire in the field of the related art.

However, none of the references reflects on following technological idea in producing and manufacturing the guide wire.

Upon imparting mechanical procedures to the core wire in order to satisfy physical properties needed for the guide wire, the stainless steel wire is deeply drawn as a highly wrought-out procedure. Upon providing the stainless steel wire with the mechanical procedures, observed is a thermal influence on the tensile strength characteristic of the core wire.

Considering a relationship between the mechanical procedures and the heat treatment in low temperature each time when the stainless steel wire is subjected to manufacturing procedures characteristic of the guide wire, accumulated are the procedures effective in increasing the tensile strength of the core wire in order to produce the guide wire with an increased tensile strength.

Therefore, the present invention has been made with the above drawbacks in mind, it is a main object of the invention to provide a medical guide wire and a method of making the same which enables an operator to use safely by attaining the most preferable tensile strength characteristic of the core wire in relation to mechanical procedures, to which the core wire is subjected, while considering the thermal influence on the tensile strength of the core wire when the austenitic stainless steel wire is deeply drawn as a highly wrought-out procedure upon forming the core wire.

SUMMARY OF THE INVENTION

According to the present invention, there is provided a medical guide wire having a core wire formed of a flexible elongate member. A helical spring body is inserted to a distal end portion of the core wire to be placed around the core wire, and a head plug is provided at distal end tips of both the core wire and the helical spring body by means of a welding member. A synthetic layer is coated at least on an outer surface of a proximal portion of the core wire. The core wire is made of austenitic stainless steel wire treated with a solid solution procedure, and drawn at a wire-drawing procedure and then heat treated at low temperature of 400° C.-495° C. A final wire-drawing procedure is defined after repeating at least more than a single set of procedures with a combination of the wire-drawing procedure and the heat-treating procedure as the single set. The core wire is rendered with a whole cross sectional reduction ratio as 90%-97.6% until the core wire is subjected to the final wire-drawing procedure. The core wire has 8% or more as a total increase rate of a tensile rupture strength attained due to the heat treatment procedure until the core wire is subjected to the final wire-drawing procedure. The core wire is subjected to predetermined turns of twist at low temperature of 380° C.-495° C. due to an electrical resistance caused by energizing the core wire after finishing the final wire-drawing procedure. The core wire is heat treated at low temperature of 340° C.-420° C. with the use of a heat generated when the synthetic layer is coated on the outer surface of the core wire after treating the distal end portion of the core wire with a mechanical procedure including grinding or pressing procedure. The core wire has 2% or more as a total increase rate of a tensile rupture strength attained each time when the core wire is subjected to the heat treatment procedure after the core wire is subjected to the final wire-drawing procedure. The core wire has 10% or more as a total increase rate of a tensile rupture strength attained each time when the core wire is subjected to the heat treatment procedure.

With the structure raised above, it becomes possible to accumulate the procedures effective in increasing the tensile strength of the core wire in order to produce the guide wire with an increased tensile strength by considering a relationship between the mechanical procedures and the heat treatment in low temperature each time when the stainless steel wire is subjected to manufacturing procedures characteristic of the guide wire.

With the core wire subjected to predetermined turns of twist at low temperature of 380° C.-495° C. due to an electrical resistance caused by energizing the core wire, it is possible to increase the straightness or linearity of the core wire even when the core wire is drawn with the whole cross sectional reduction ratio as 90%-97.6%, while at the same time, preventing the disconnection of the core wire in the twisting procedure so as to maintain its quality stable.

According to other aspect of the present invention, among the predetermined turns of twist, to which the core wire is subjected at low temperature of 380° C.-495° C. due to the electrical resistance caused by energizing the core wire. The twisting procedure accompanies the heat treatment, a temperature of which progressively increases with an increase of twisting turns of the core wire. The heat treatment is due to the electrical resistance caused by energizing the core wire at low temperature of 380° C.-495° C. (maximum temperature).

Such is the structure that upon using the core wire drawn with the whole cross sectional reduction ratio as 90%-97.6%, the core wire has a crystalline texture more minutely rendered with the increase of twisting turns of the core wire, and residual stresses are removed from the core wire by subjecting the core wire to the heat treatment, a temperature of which progressively increases with the increase of twisting turns of the core wire.

This also decreases a structural inequality between an outer layer and an inner layer of the core wire so as to homogenize an internal texture of the core wire, and preventing the core wire from being disconnected in the twisting procedure, thereby insuring a high tensile rupture strength with a high straightness so as to maintain the product quality stable.

According to other aspect of the present invention, a heat treatment procedure at low temperature is provided to heat treat the core wire at 400° C.-495° C. after treating the distal end portion of the core wire with the mechanical procedure, but before coating the synthetic layer on the core wire. The tensile rupture strength increases compared to the tensile rupture strength after the mechanical procedure is implemented. The core wire has 11.5% or more as a total increase rate of the tensile rupture strength attained each time when the core wire is subjected to the heat treatment.

According to other aspect of the present invention, the distal end portion of the core wire is ground, so that a ground portion of the core wire is heat treated at low temperature and the ground portion is pressed. At least a pressed portion of the core wire is heat treated at low temperature of 180° C.-300° C. due to a heat generated when coating the synthetic layer on the helical spring body. A tensile rupture strength of the ground portion or the pressed portion of the core wire increases compared to the tensile rupture strength which the distal end portion of the core wire has before being heat treated at low temperature of 180° C.-300° C. when coating the synthetic layer on the helical spring body.

According to other aspect of the present invention, the core wire is rendered with a whole cross sectional reduction ratio as 94%-97.6% until the core wire is subjected to the final wire-drawing procedure. This makes it possible to significantly increase a tensile rupture strength of the core wire.

Since the core wire is twisted while being heat treated at low temperature due to the electrical resistance caused by energizing the core wire, it is possible to significantly increase the tensile rupture strength compared to the case in which the core wire simply heat treated at low temperature but not twisted, thereby providing a high tensile rupture strength with the medical guide wire. In this situation, the core wire abruptly changes the tensile rupture strength with the cross sectional reduction ratio 94% as a boundary.

According to other aspect of the present invention, there is provided a method of making a medical guide wire having a core wire formed of a flexible elongate member. A helical spring body is inserted to a distal end portion of the core wire to be placed around the core wire. A head plug is provided at distal end tips of both the core wire and the helical spring body by means of a welding member. The core wire is made of austenitic stainless steel wire treated with a solid solution procedure, and drawn at a wire-drawing procedure and then heat treated at low temperature of 400° C.-495° C. for 10-180 minutes. A final wire-drawing procedure is defined after repeating at least more than a single set of procedures with a combination of the wire-drawing procedure and the heat-treating procedure as the single set. The core wire is rendered with a whole cross sectional reduction ratio as 90%-97.6% until the core wire is subjected to the final wire-drawing procedure. One end of the core wire is twisted around its axis by 100-275 turns per meter with the other end loaded by a tensile weight, a magnitude of which is 5%-30% of a tensile rupture strength before the core wire is twisted under the condition that the core wire is heat treated at low temperature of 380° C.-495° C. for 0.5-60 minutes due to an electrical resistance caused by energizing the core wire. The distal end portion of the core wire is ground or pressed after ground. The helical spring body is inserted to the distal end portion of the core wire to place the helical spring body around the distal end portion of the core wire. The core wire and the helical spring body are partly secured together by means of the welding member. The head plug is formed by welding the distal end tips of both the core wire and the helical spring body by means of the welding member.

Such is the structure that the core wire is heat treated at low temperature after the core wire is drawn in the first heat treating procedure, and then the core wire is heat treated at low temperature after the core wire is twisted in the second heat treating procedure. This makes it possible to remove the residual stresses from the core wire each in the first and second heat treating procedure, thus providing a high tensile strength with the core wire of the medical guide wire.

According to other aspect of the present invention, the core wire is further heat treated at low temperature of 400° C.-495° C. for 10-180 minutes after one end of the core wire is twisted, but before the distal end portion of the core wire is ground or pressed after ground.

According to other aspect of the present invention, a synthetic layer is coated at least on an outer surface of the helical spring body after the distal end portion of the core wire is ground or pressed after ground. Thereafter, at least a ground portion or a pressed portion of the distal end portion of the core wire is heat treated at low temperature of 340° C.-420° C. for 10-180 minutes before inserting the helical spring body to the distal end portion of the core wire.

According to other aspect of the present invention, the predetermined turns of twist has a first twisting procedure in which one end of the core wire is twisted around its axis by 100-275 turns per meter after the final wire-drawing procedure with the other end loaded by a tensile weight, a magnitude of which is 5%-30% of a tensile rupture strength before the core wire is twisted, and a second twisting procedure in which the core wire is subjected to heat treatment, a temperature of which progressively increases with an increase of the turns of twist by the electrical resistance caused by energizing the core wire at low temperature of 380° C.-495° C. as a maximum temperature.

Such is the structure that the core wire has a crystalline texture more minutely rendered with the increase of twisting turns of the core wire, and residual stresses are removed from the core wire by subjecting the core wire to the heat treatment, a temperature of which progressively increases with the increase of twisting turns of the core wire.

This also decreases structural inequality between an outer layer and an inner layer of the core wire so as to homogenize an intermetallic texture of the core wire, and preventing the core wire from being disconnected in the twisting procedure, thereby providing the core wire with a high tensile rupture strength and a high straightness so as to maintain the product quality stable for the medical guide wire.

According to other aspect of the present invention, the other end of the core wire is twisted by 100-200 turns per meter. This makes it possible to decreases the structural inequality between the outer layer and the inner layer of the core wire so as to homogenize the internal texture of the core wire, and significantly decreasing residual angles of the core wire after the core wire is manipulatively bent, thereby providing a high tensile rupture strength and high straightness with the core wire so as to maintain the product quality stable upon manufacturing the medical guide wire.

According to other aspect of the present invention, after welding the core wire and the helical spring body together by means of the welding member, a synthetic layer is coated on an outer surface of the helical spring body. At least the distal end portion of the core wire is heat treated at low temperature of 180° C.-300° C. for ⅙-60 minutes within the helical spring body by using a heat generated upon coating the synthetic layer on the helical spring body.

The structure is such that it is possible to provide a high tensile rupture strength and high straightness with the core wire as mentioned above.

According to other aspect of the present invention, the welding member is formed by a eutectic alloy having a melting point of 180° C.-495° C.

Upon welding the core wire and the helical spring body by means of the welding member, it becomes possible to increase the tensile rupture strength of the core wire by making use of the melting heat produced from the welding member. This means to increase the tensile rupture strength of the core wire at a welded portion between the core wire and the head plug. This holds true at a welded portion between the core wire and an intermediary sections which are intermittently provided between the helical spring body and the core wire.

According to other aspect of the present invention, there is provided an assembly of a microcatheter and a guiding catheter combined with the medical guide wire. An outer diameter of the medical guide wire measures 0.228 mm-0.254 mm (0.009 inches-0.010 inches) which is inserted into the microcatheter, an inner diameter of which measures 0.28 mm-0.90 mm, and the medical guide wire inserted into the microcatheter is further inserted into the guiding catheter, an inner diameter of which ranges 1.59 mm to 2.00 mm.

With the microcatheter, the guiding catheter and the medical guide thus manufactured, it is possible to make the assembly substantially thin so as to be well-suited for holding a minimally intrusive surgery.

According to other aspect of the present invention, there is provided an assembly of a balloon catheter and a guiding catheter combined with the medical guide wire. An outer diameter of the medical guide wire measures 0.228 mm-0.254 mm (0.009 inches-0.010 inches) which is inserted into the balloon catheter, an inner diameter of which measures 0.28 mm-0.90 mm, and the medical guide wire inserted into the balloon catheter is further inserted into the guiding catheter, an inner diameter of which ranges 1.59 mm to 2.00 mm.

With the balloon catheter, the guiding catheter and the medical guide thus manufactured, it is possible to make the assembly substantially thin so as to be well-suited for holding a minimally intrusive surgery in the same manner as mentioned above.

BRIEF DESCRIPTION OF THE DRAWINGS

A preferred form of the present invention is illustrated in the accompanying drawings in which.

DETAILED DESCRIPTION OF PREFERRED EMBODIMENTS

Figure 1:
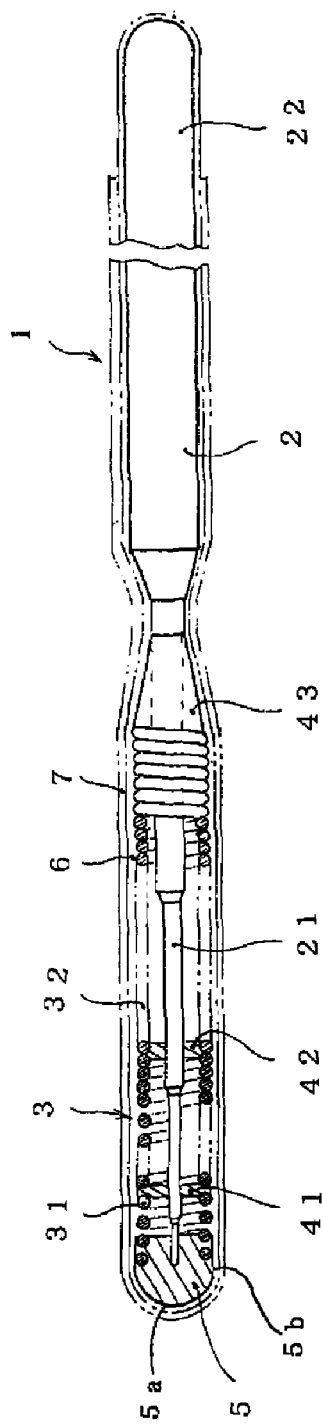
FIG. 1 is a plan view of a medical guide wire but partly sectioned according to a first embodiment of the invention.

In the following description of the depicted embodiments, the same reference numerals are used for features of the same type.

Figure 2:
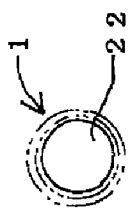
FIG. 2 is a right side elevational view of the medical guide wire.

Referring to FIGS. 1 through 6 which show a medical guide wire 1 (referred to as a guide wire 1 hereinafter) according to a first embodiment of the invention. The guide wire 1 has a core wire 2 formed by a flexible elongate member. The core wire 2 has a distal end portion 21, around which a helical spring body 3 is coaxially placed as shown in FIGS. 1, 2.

The helical spring body 3 (simply referred to as a spring body 3 hereinafter) has a distal end portion as a radiopaque coil 31 which is made of silver, platinum, wolfram or the like.

At a front welding section 41, a middle welding section 42 and a rear welding section 43 each designated by the distal end portion 21 of the core wire 2, the core wire 2 and the spring body 3 are partly secured by means of a welding member 4.

At a distal extremity of the core wire 2, a head plug 5 is provided which is made of the welding member 4 to connectedly secure the spring body 3 to the core wire 2. The head plug 5 has a semi-spherical portion 5a integrally formed with a short cylindrical portion 5b.

Figure 3:
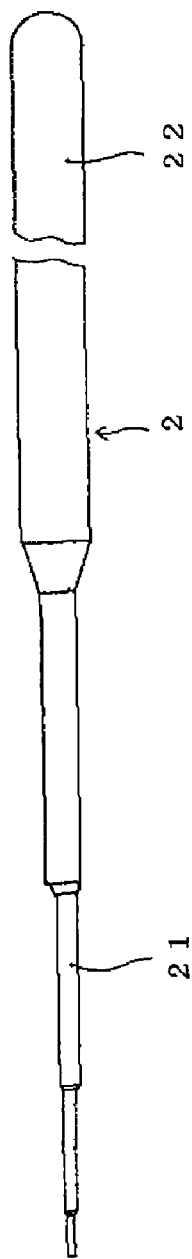
FIG. 3 is a plan view of a core wire.
Figure 5:
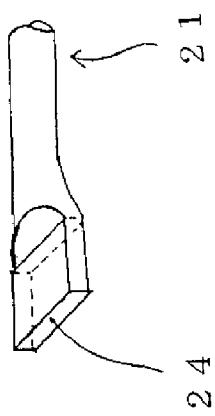
FIGS. 5 and 6 are perspective views each showing a distal end portion of the core wire.
Figure 6:
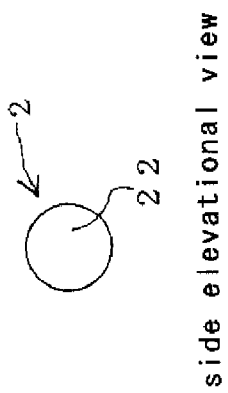
Figure 4:
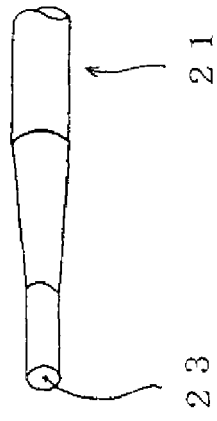
FIG. 4 is a right side elevational view of the core wire.

As clearly shown in FIGS. 3, 4, the core wire 2 measures around 0.060 mm-0.200 mm in diameter and extends by about 300 mm from the distal extremity of the core wire 2.

The rest of the core wire 2 corresponds to a proximal portion 22 made of thicker coil line elements extending approximately 1200 mm-2700 mm.

The distal end portion 21 has a diameter-reduced section, a diameter of which decreases progressively as approaching forward. The diameter-reduced tip section may be circular, square or rectangular in cross section as observed at numerals 23, 24 in FIGS. 5, 6.

On an outer surface of the proximal end portion 22 of the core wire 2, coated is a synthetic layer 6 which is made of polyurethane, fluorocarbon resin (e.g., PTFE) or other polymers. On an outer surface of the spring body 3, coated is a synthetic resin layer which is formed by, for example, polyurethane. The synthetic layer tightly covers an outer surface of the front end portion 21 of the core wire 2.

The synthetic layer has an outer surface coated with a hydrophilic polymer 7 as a lubricant (e.g., polyvinylpyrrolidone) which exhibits the lubricity when moistened.

The core wire 2 is made of austenitic stainless steel wire treated as a solid solution, and drawn with a whole cross sectional reduction ratio R as 90%-97.6%.

The whole cross sectional reduction ratio R means a reduction rate expressed by $R=(S1-S2)/S1$.

Where S1 is a cross sectional area regarding the original diameter of the solid solution wire before the wire is drawn, and S2 is a resultant cross sectional area regarding the finished diameter of the solid solution wire after the wire is drawn.

Figure 14:
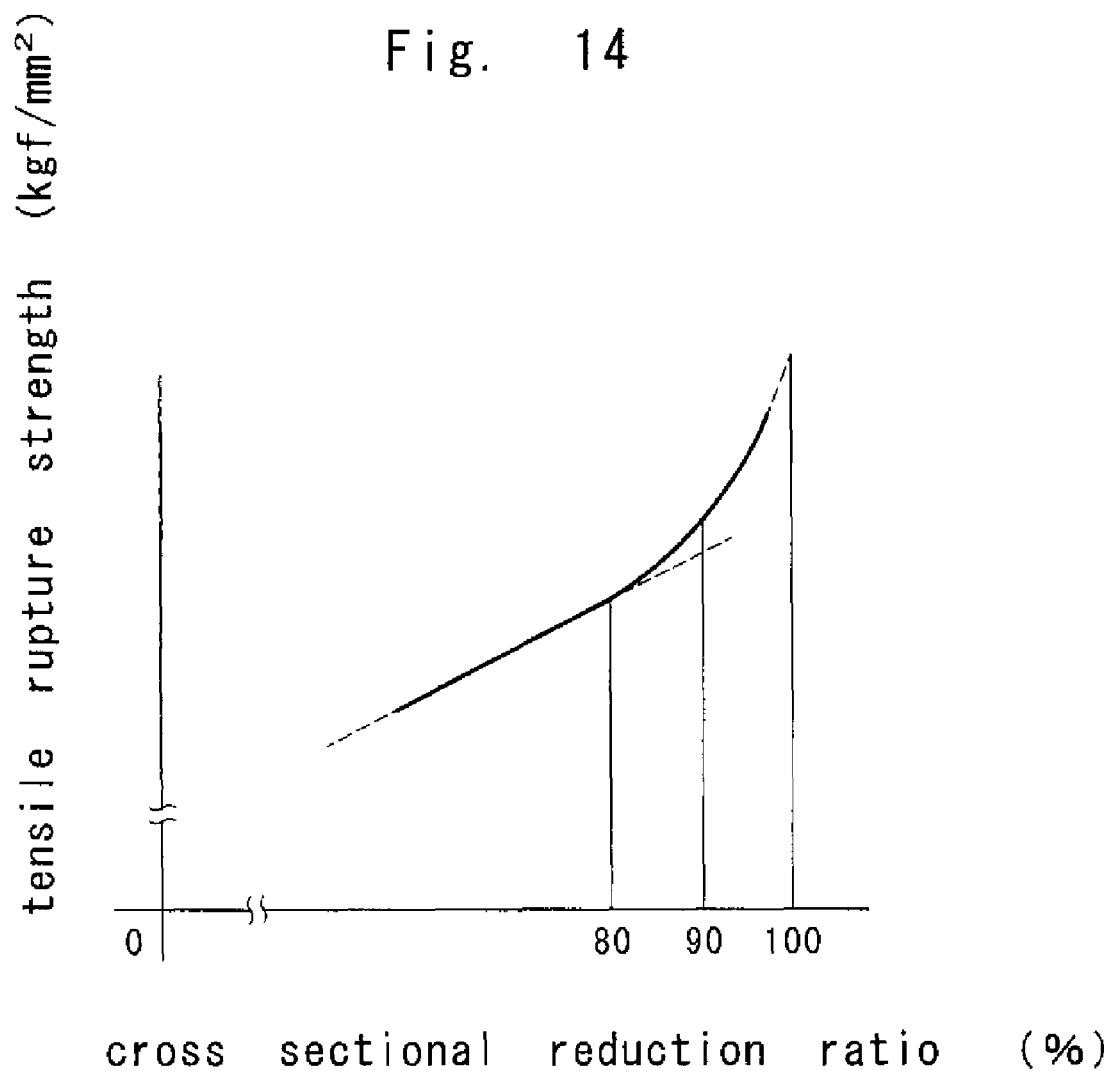
FIG. 14 is a graphical representation of a tensile strength characteristic showing a relationship between a whole cross sectional reduction ratio and a tensile rupture strength.

The whole cross sectional reduction ratio is determined to be 90% or more because the tensile rupture strength changes at the ratio R of 80, and abruptly increases when the ratio R goes beyond 90% as depicted in FIG. 14.

This is because the austenitic stainless steel wire is plastically wrought out tightly during the drawing procedure, so that the stainless steel wire develops a fibroid structure exceedingly when the ratio R goes beyond 90%.

The whole cross sectional reduction ratio is determined to be 97.6% or less because the austenitic stainless steel wire comes to develop minute voids within its structure to make the structure brittle when the ratio exceeds 97.6% as an upper limit.

That the austenitic stainless steel wire is drawn as the solid solution, is to provide the wire with superior workability.

Since it is hard to obtain the minute crystalloid of the austenitic stainless steel wire by making use of the transmutational point during the heat treatment process, instead of the heat treatment, the cold working process is used in order to achieve the minute crystalloid of the austenitic stainless steel wire, and the wire is work hardend to improve the tensile strength during the drawing process.

Another reason to use the austenitic stainless steel wire is that the martensitic stainless steel wire tends to be hardened during the quenching process, and the ferro stainless steel wire tends to be hot-short (sigma brittle, brittle at 475° C.).

Table 1 shows a tensile strength characteristic depicting a relationship between a whole cross sectional reduction ratio and a tensile rupture strength of the austenitic stainless steel wire treated as a solid solution.

The austenitic stainless steel wire (1.5 mm in diameter) is rendered as a matrix wire to be 68 kgf/mm$^2$ in tensile rupture strength, and drawn (primary drawing procedure).

Then, the stainless steel wire is heat treated at low temperature (420° C.) for 75 minutes (primary low heat treatment) within a thermal atmosphere in a furnace heated in the range of 400° C.-495° C. for 10-180 minutes.

The stainless steel wire is further drawn (secondary drawing procedure) to have 90% (first embodiment) and 94% (second embodiment) as the whole cross sectional reduction ratio, and heat treated at low temperature (450° C.) again for 120 minutes (secondary low heat treatment) in the same furnace used in the primary low heat treatment.

Thereafter, the distal end portion 21 of the core wire 2 is ground to have 0.150 mm in outer diameter. On the proximal end portion of the core wire 2, the synthetic layer is coated by spraying the fluorocarbon resin (e.g., PTF E) thereon, and is dried and sintered in a thermal atmosphere (340° C.-420° C.) for 10-180 minutes (e.g., 385° C. for 30 minutes as a tertiary low heat treatment) while considering the thermal influence on the tensile strength characteristic of the core wire. The items in Table 1 are graphically represented by items in FIG. 7. The low heat treatment used herein is tantamount to being heat treated at low temperature.

The tensile rupture stress is represented by $Rp=P1/Sp$. Where P1 is a magnitude of a tensile force applied when the wire surrenders to disconnection, and Sp is a cross sectional area of the wire when the wire surrenders to disconnection.

TABLE 1

| Procedure | Embodiment 1 | Embodiment 2 |
|---|---|---|
| matrix: diameter (mm) | 1.5 | 1.5 |
| tensile rupture strength (kgf/mm2) | 68 | 68 |
| primary drawing diameter (mm) | 0.53 | 0.48 |
| reduction ratio (%) | 87.5 | 89.8 |
| tensile rupture strength (kgf/mm2) | 215 | 226 |
| primary low heat treatment temp. time | 420° C. for 75 min. | 420° C. for 75 min. |
| tensile rupture strength (kgf/mm2) | 242 | 256 |
| (1) increase rate (%) | 12.6 | 13.3 |
| secondary drawing diameter (mm) | 0.475 | 0.367 |
| reduction ratio (%) | 19.7 | 41.5 |
| tensile rupture strength (kgf/mm2) | 252 | 269 |

TABLE 1-continued

| Procedure | Embodiment 1 | Embodiment 2 |
|---|---|---|
| secondary low heat treatment temp. time | 450° C. for 120 min. | 450° C. for 120 min. |
| tensile rupture strength (kgf/mm2) | 256 | 276 |
| (2) increase rate (%) | 1.6 | 2.6 |
| mechanical procedure | grinding | grinding |
| diameter (mm) | 0.150 | 0.150 |
| tertiary low heat treatment temp. time | 385° C. for 30 min. | 385° C. for 30 min. |
| tensile rupture strength (kgf/mm2) | 259 | 280 |
| (3) increase rate (%) | 1.2 | 1.4 |
| whole cross sectional reduction ratio (%) | 90 | 94 |
| total increase rate {(2) + (3)} (%) | 2.8 | 4.0 |
| total increase rate {(1) + (2) + (3)} (%) | 15.4 | 17.3 |

According to Table 1, the core wire shows 12.6% (in the first embodiment of the invention) and 13.3% (in the second embodiment of the invention) as an increase rate of the tensile rupture strength at the primary low heat treatment, but before implementing the secondary drawing procedure (final drawing procedure).

After completing the final drawing procedure at the respective low heat treatment, a total increase rate ((1)+(2)) of the tensile rupture strength comes to 2.8% (in the first embodiment of the invention) and 4.0% (in the second embodiment of the invention), and a resultant total increase rate ((1)+(2)+(3)) of the tensile rupture strength comes to 15.4% (in the first embodiment of the invention) and 17.3% (in the second embodiment of the invention).

Especially when the distal end portion of the core wire is mechanically ground to form a ground portion (0.150 mm in diameter), the tensile rupture strength of the ground portion increases by 53 gf from 4.522 gf to 4.575 gf calculated in terms of a cross sectional area in the first embodiment of the invention. In the second embodiment of the invention, the tensile rupture strength of the ground portion increases by approximately 71 gf.

Since the ground portion of the core wire 2 is a section navigated through the sinuous path of the coronary artery to reach a diseased area, the portion requires a sufficient tensile strength and fatigue-resistant property against repetitive bending manipulations. Considering that the number of cyclic endurance is represented by stress endurance diagram (S-N diagram), even a small increase of the tensile strength leads to a remarkable result of the number of cyclic endurance.

The stainless steel wire is heat treated in the furnace within the range of 400° C.-495° C. for 10-180 minutes after completing the primary drawing procedure. This is to consider a characteristic of the tensile strength (FIG. 13) influenced by heat upon drawing the austenitic stainless steel wire, in addition to the productivity in the drawing process and a way to maintain the product quality stable.

The stainless steel wire is further treated at low temperature (secondary low heat treatment) within the range of 400° C.-495° C. for 10-180 minutes after completing the final drawing procedure. This is to consider the characteristic of the tensile strength (FIG. 13) influenced by heat upon drawing the austenitic stainless steel wire, in addition to the productivity in the drawing process within the furnace and a way to maintain the product quality stable.

The stainless steel wire is still further treated at low temperature (tertiary low heat treatment) in the range of 340° C.-420° C. for 10-180 minutes after the end of the grinding procedure. This is to consider the characteristic of the tensile strength (FIG. 13) improved by heat upon drawing the austenitic stainless steel wire when drying and sintering the synthetic layer (e.g., PTFE) coated on the proximal end portion 22 of the core wire 2, in addition to the productivity in the tertiary low heat treatment and a way to maintain the product quality stable.

Upon forming the core wire 2 from the austenitic stainless steel wire, five sets or more may be repetitively implemented with a combination of the low heat treatment and the drawing procedure as a single set. However, it is preferable to repeat three sets or less from the economical and productive point of view.

As for the whole cross sectional reduction ratio, the ratio in the primary drawing procedure may be greater than the ratio in the secondary drawing procedure, and vice versa.

However, by predetermining the ratio to be higher (87.5%-94.2%) in the primary drawing procedure as observed in the embodiments of the invention, it becomes possible to increase the martensitic component so as to suppress the crystalline growth of the stainless steel due to the heat treatment procedure. From the economical and productive point of view, it is preferable to predetermine the ratio to be higher in the primary drawing procedure than in the subsequent drawing procedure.

In order to further improve the tensile rupture strength due to the growth of the martensitic component, it is preferable to set the working temperature at 140° C. or less which corresponds to the temperature of an outer surface of the core wire in the drawing procedure. This is achieved by setting a cooling refrigerant in a wet drawing procedure or by setting a lubricant agent sprayed in showers to working dices in the drawing procedure. Upon using the cooling refrigerant or the lubricant agent, it becomes possible to adjust a temperature of the cooling refrigerant or temperature of the lubricant agent.

According to Table 2 which exhibits the tensile strength characteristic, the core wire shows 94.8% (in the third embodiment of the invention), 96% (in the fourth embodiment of the invention) and 97.6% (in the fifth embodiment of the invention) as the whole cross sectional reduction ratio in the drawing procedure, and the core wire is heat treated at 380° C.-495° C. by its electrical resistance (approx. 1.8 ampere) for ½-60 minutes (e.g., 450° C. for 5 min.) while twisted in the low heat treatment under the predetermined condition.

Thereafter, the distal end portion 21 of the core wire 2 is mechanically ground to form the ground portion which is subjected to the low heat treatment at the temperature of 340° C.-420° C. for 10-180 minutes (e.g., 385° C. for 30 min.) in the thermal atmosphere due to the furnace without using the heat due to the electrical resistance. Save the above low heat treatment, the other procedures used above are the same as used in the first and second embodiments of the invention. As described hereinafter in detail, the core wire 2 is twisted under the tensile weight 12. The tensile weight 12 is tantamount to 10%-30% (e.g., 20%) of the tensile rupture strength which the core wire 2 has before subjected to the twisting procedure.

tensile rupture strength comes to 17.6% (in the third embodiment of the invention), 21.2% (in the fourth embodiment of the invention) and 20.2% (in the fifth embodiment of the invention).

Figure 8:
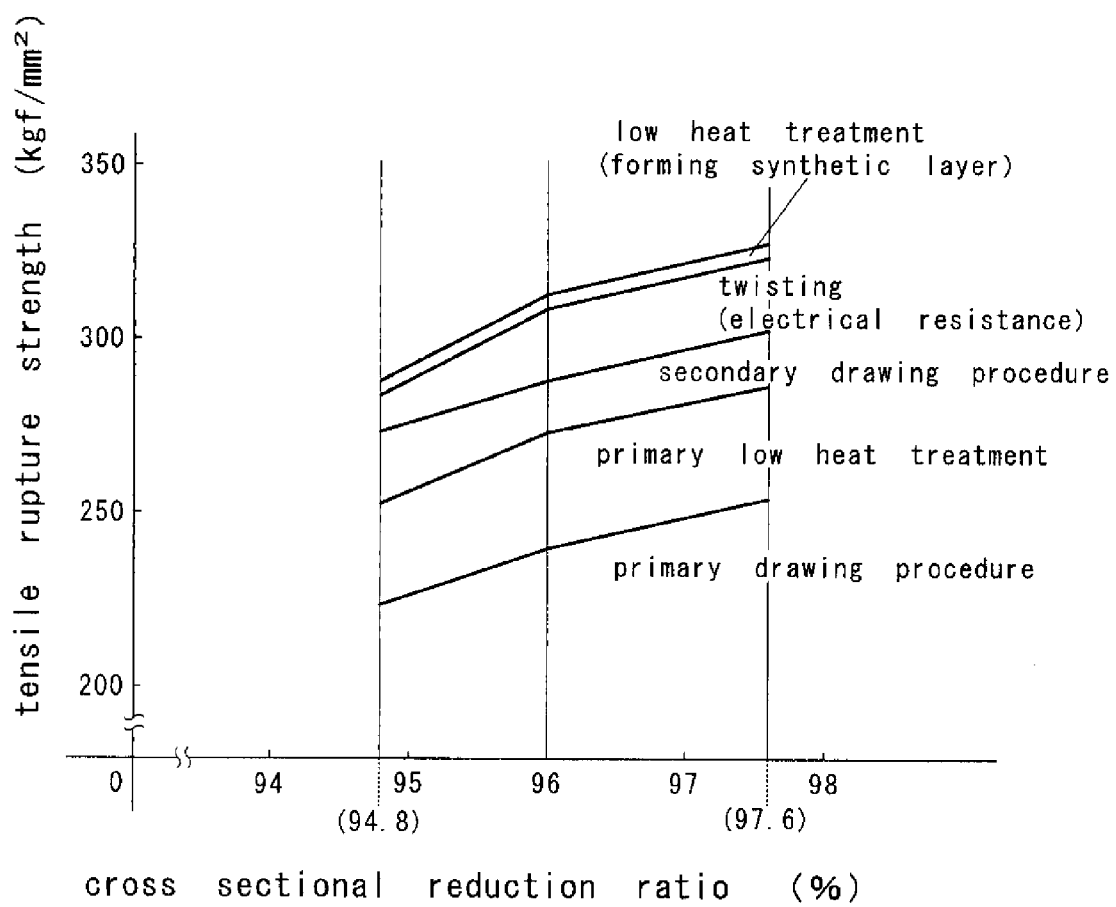
FIG. 8 is a graphical representation of a tensile strength characteristic showing a relationship between a whole cross sectional reduction ratio and a tensile rupture strength according to a sixth, seventh and eighth embodiment of the invention.

As observed in FIG. 8 which graphically represents the items denoted in Table 2, the core wire shows increase rates higher than those of the first and second embodiments of the invention particularly upon twisting the core wire under the condition that the core wire is heat treated due to its electrical resistance when energized.

This is because the core wire is twisted, so that the lay appears obliquely against its axis in addition to being tightly drawn lengthwisely along the axis. This decreases a structural inequality which the core wire has between an outer layer of higher hardness and an inner layer of lower hardness, thereby

TABLE 2

| Procedure | Embodiment 3 | Embodiment 4 | Embodiment 5 |
|---|---|---|---|
| matrix: diameter (mm) | 1.5 | 1.5 | 1.5 |
| tensile rupture strength (kgf/mm2) | 68 | 68 | 68 |
| primary drawing diameter (mm) | 0.50 | 0.41 | 0.36 |
| reduction ratio (%) | 88.9 | 92.5 | 94.2 |
| tensile rupture strength (kgf/mm2) | 224 | 240 | 254 |
| primary low heat treatment temp. time | 420° C. for 75 min. | 420° C. for 75 min. | 420° C. for 75 min. |
| tensile rupture strength (kgf/mm2) | 252 | 272 | 286 |
| (1) increase rate (%) | 12.5 | 13.3 | 12.6 |
| secondary drawing diameter (mm) | 0.340 | 0.300 | 0.228 |
| reduction ratio (%) | 53.8 | 46.5 | 59.9 |
| tensile rupture strength (kgf/mm2) | 272 | 288 | 302 |
| twist under electrical resistance temp. time | 450° C. for 5 min | 450° C. for 5 min. | 450° C. for 5 min. |
| turns of tiwst | 120 turns/m | 120 turns/m | 120 turns/m |
| tensile rupture strength (kgf/mm2) | 283 | 308 | 323 |
| (2) increase rate (%) | 4.0 | 6.9 | 7.0 |
| mechanical procedure | grinding | grinding | grinding |
| diameter (mm) | 0.150 | 0.150 | 0.150 |
| low heat treatment (synthetics) temp. time | 385° C. for 30 min. | 385° C. for 30 min. | 385° C. for 30 min. |
| tensile rupture strength (kgf/mm2) | 286 | 311 | 325 |
| (3) increase rate (%) | 1.1 | 1.0 | 0.6 |
| whole cross sectional reduction ratio (%) | 94.8 | 96.0 | 97.6 |
| total increase rate {(2) + (3)} (%) | 5.1 | 7.9 | 7.6 |
| total increase rate {(1) + (2) + (3)} (%) | 17.6 | 21.2 | 20.2 |

According to Table 2, the core wire shows 12.5% (in the third embodiment of the invention), 13.3% (in the fourth embodiment of the invention) and 12.6% (in the fifth embodiment of the invention) as an increase rate of the tensile rupture strength at the primary low heat treatment, but before implementing the secondary drawing procedure (final drawing procedure).

After completing the final drawing procedure at the respective low heat treatment, a total increase rate ((2)+(3)) of the tensile rupture strength comes to 5.1% (in the third embodiment of the invention), 7.9% (in the fourth embodiment of the invention) and 7.6% (in the fifth embodiment of the invention), and a resultant total increase rate ((1)+(2)+(3)) of the homogenizing an internal texture of the core wire to an acceptable degree so as to remove residual stresses locally developed in the core wire.

Figure 13:
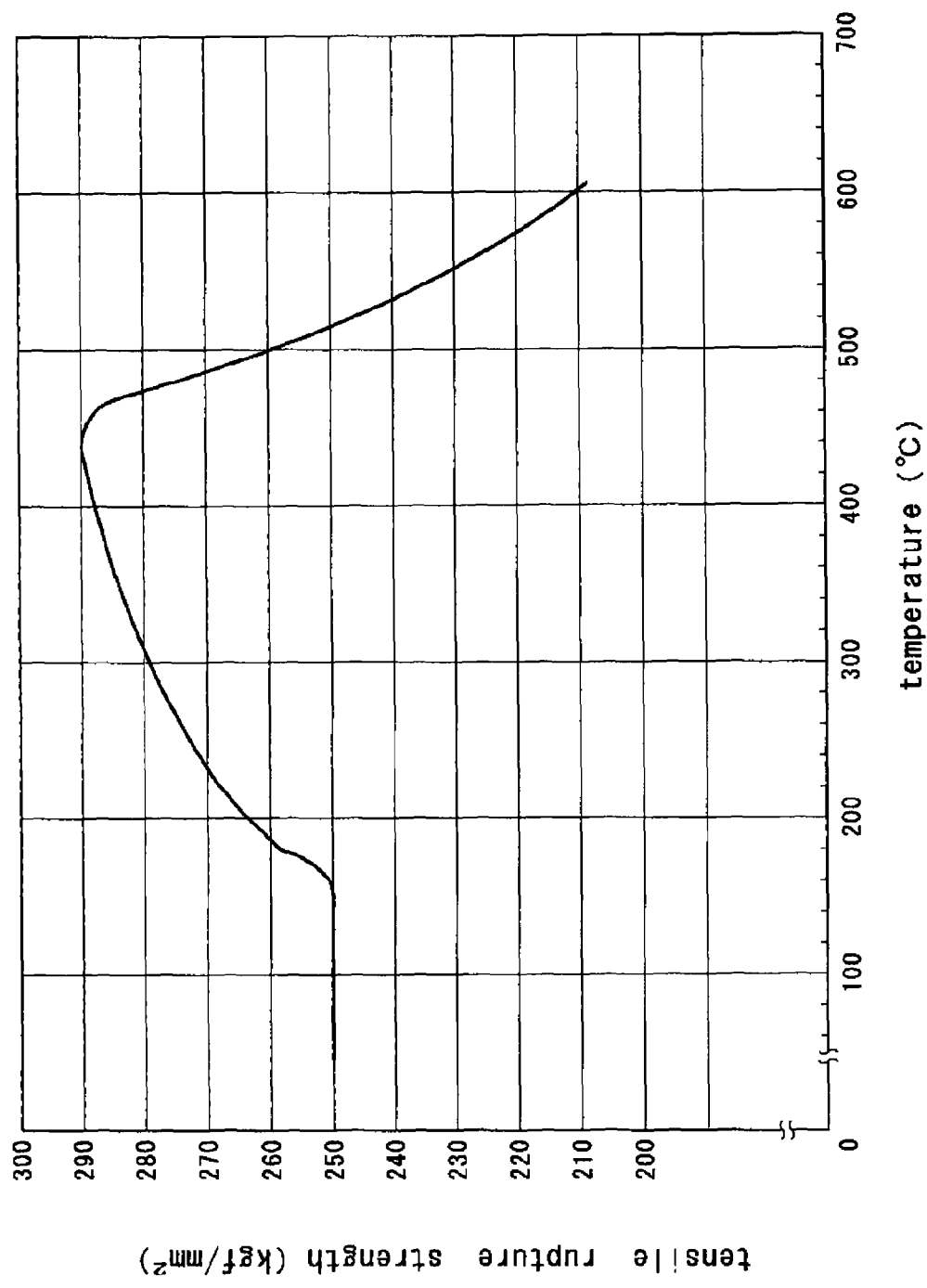
FIG. 13 is a graphical representation of a characteristic curve showing a relationship between the tensile strength and the temperature of the core wire.

The core wire is processed at 380° C.-495° C. in the low heat treatment due to the electrical resistance of the core wire. This is determined by considering a tensile strength characteristic due to the temperature of the austenitic stainless steel wire being tightly drawn as shown in FIG. 13, and a residual angle left upon subjecting the core wire to a bending experimentation test after twisted as described hereinafter in FIG. 11.

The core wire is heated for ½-60 minutes because it is insufficient to improve the tensile strength when the heating time period becomes lower than ½ minutes, and the curve of the tensile strength substantially forms a plateau and no remarkable improvement is expected in the tensile strength when the heating time period exceeds 60 minutes.

According to Table 3, the core wire is heated at 400° C.-495° C. for 10-180 minutes (e.g., 450° C. for 120 minutes) within the furnace in the low heat treatment after the core wire is twisted due to the electrical resistance under the predetermined conditions. After grinding the distal end portion 21 of the core wire 2, the core wire 2 is treated in the same manner as observed from the first to the fifth embodiments of the invention.

In Table 3, it is to be noted that the items from the sixth to eighth embodiments of the invention correspond to those from the third to fifth embodiments of the invention.

the invention), and a resultant total increase rate ((1)+(2)+(3)+(4)) of the tensile rupture strength comes to 18.9% (in the sixth embodiment of the invention), 22.5% (in the seventh embodiment of the invention) and 21.7% (in the eighth embodiment of the invention. These are the highest increase rate achieved each in the sixth to eighth embodiments of the invention.

This is because the core wire is tightly twisted so that the lay appears obliquely against its axis, and tightly drawn lengthwisely along the axis. This decreases an inequality of the hardness distribution between the outer layer and the inner layer of the core wire, thereby homogenizing the internal texture of the core wire to an acceptable degree.

This is realized by grasping the characteristic of the tensile rupture strength depending on the temperature when tightly

TABLE 3

| Procedure | Embodiment 6 | Embodiment 7 | Embodiment 8 |
|---|---|---|---|
| matrix: diameter (mm) | 1.5 | 1.5 | 1.5 |
| tensile rupture | 68 | 68 | 68 |
| primary drawing diameter (mm) | 0.50 | 0.41 | 0.36 |
| reduction ratio (%) | 88.9 | 92.5 | 94.2 |
| tensile rupture strength (kgf/mm2) | 224 | 240 | 254 |
| primary low heat treatment temp. time | 420° C. for 75 min. | 420° C. for 75 min. | 420° C. for 75 min. |
| tensile rupture strength (kgf/mm2) | 252 | 272 | 286 |
| (1) increase rate (%) | 12.5 | 13.3 | 12.6 |
| secondary drawing diameter (mm) | 0.340 | 0.300 | 0.228 |
| reduction ratio (%) | 53.8 | 46.5 | 59.9 |
| tensile rupture strength (kgf/mm2) | 272 | 288 | 302 |
| twist under electrical resistance temp. time | 450° C. for 5 min. | 450° C. for 5 min. | 450° C. for 5 min. |
| turns of tiwst | 120 turns/m | 120 turns/m | 120 turns/m |
| tensile rupture strength (kgf/mm2) | 283 | 308 | 323 |
| (2) increase rate (%) | 4.0 | 6.9 | 7.0 |
| secondary low heat treatment temp. time | 450° C. for 120 min. | 450° C. for 120 min. | 450° C. for 120 min. |
| tensile rupture strength (kgf/mm2) | 287 | 312 | 328 |
| (3) increase rate (%) | 1.4 | 1.3 | 1.5 |
| mechanical procedure | grinding | grinding | grinding |
| diameter (mm) | 0.150 | 0.150 | 0.150 |
| low heat treatment (synthetics) temp. time | 385° C. for 30 min. | 385° C. for 30 min. | 385° C. for 30 min. |
| tensile rupture strength (kgf/mm2) | 290 | 315 | 330 |
| (4) increase rate (%) | 1.0 | 0.96 | 0.6 |
| whole cross sectional reduction ratio (%) | 94.8 | 96.0 | 97.6 |
| total increase rate {(2)~(4)} (%) | 6.4 | 9.16 | 9.1 |
| total increase rate {(1)~(4)} (%) | 18.9 | 22.5 | 21.7 |

According to Table 3, the core wire shows the same increase rates of the tensile rupture strength as those obtained in the third to fifth embodiments of the invention before implementing the secondary drawing procedure (final drawing procedure).

After completing the final drawing procedure at the respective low heat treatment, a total increase rate ((2)+(3)+(4)) of the tensile rupture strength comes to 6.4% (in the sixth embodiment of the invention), 9.16% (in the seventh embodiment of the invention) and 9.1% (in the eighth embodiment of drawing the austenitic stainless steel wire to determine the optimal time and temperature in the low heat treatment, thereby significantly decreasing the structural inequality between the inner layer and the outer layer of the core wire so as to remove the residual stresses locally developed in the core wire.

That the core wire is heated at 380° C.-495° C. for ½-60 minutes under the low heat treatment, is in the same reasons as mentioned in the third to fifth embodiments of the invention.

Figure 7:
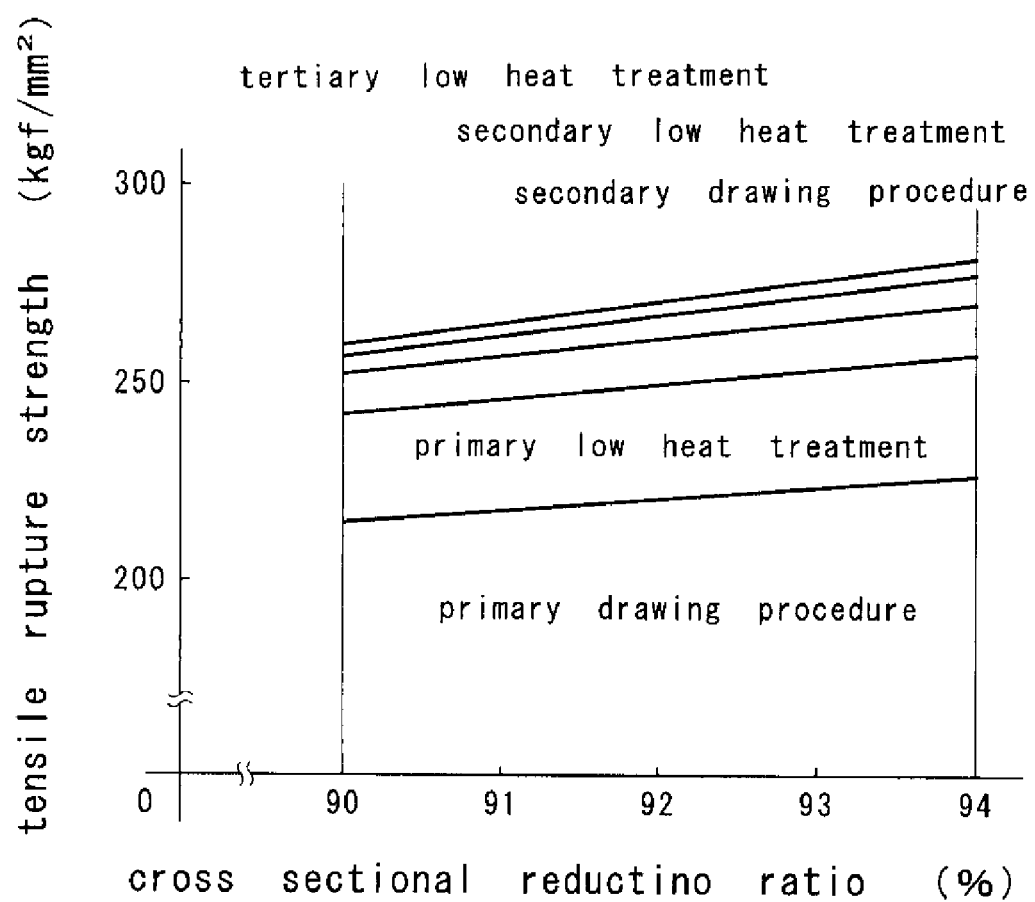
FIG. 7 is a graphical representation of a tensile strength characteristic showing a relationship between a whole cross sectional reduction ratio and a tensile rupture strength according to the first and second embodiment of the invention.
Figure 9:
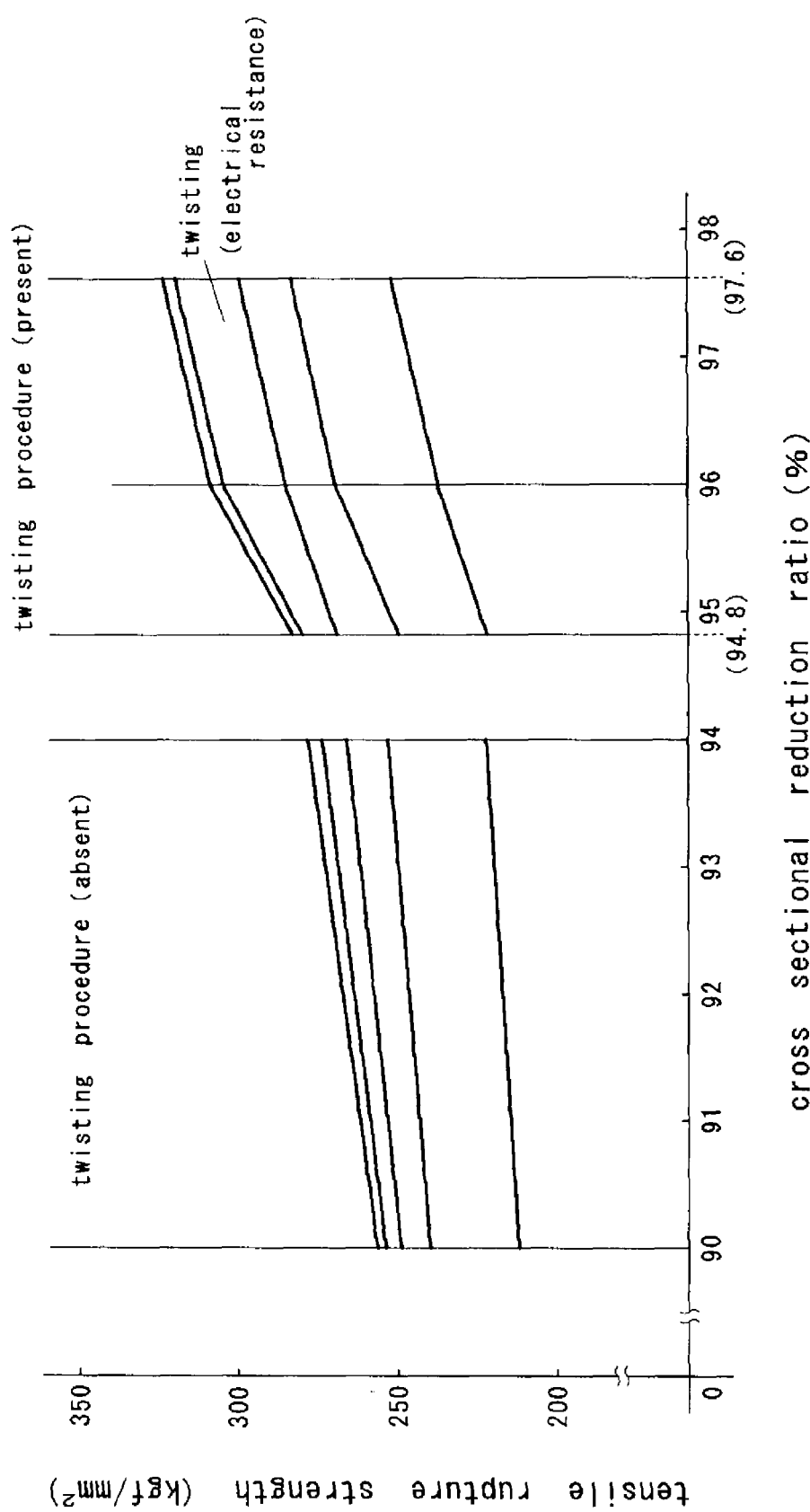
FIG. 9 is a graphical representation of a tensile strength characteristic showing a relationship between a whole cross sectional reduction ratio and a tensile rupture strength according to the first, second, sixth, seventh and eighth embodiment of the invention.

FIG. 9 is a graphical representation attained by superimposing the items in FIG. 7 over those in FIG. 8. As understood from FIG. 9, the increase rates of the tensile rupture strength are higher after the core wire is twisted under the low heat treatment due to the electrical resistance than those in which the core wire is heat treated at low temperature, but not twisted. FIG. 9 demonstrates that the increase rate of the tensile rupture strength tends to abruptly rise with the whole cross sectional reduction ratio 94% as a boundary.

During the process in which the core wire is twisted under the low heat treatment, the residual stresses developed during the twisting procedure may be removed while twisting the core wire in the low heat treatment after heating the core wire at 380° C.-495° C. by energizing the core wire.

In this situation, it is preferable to gradually heat the core wire from the room temperature (cold working temperature) to 380° C.-495° C. (maximum temperature range) as the twisting turns of the core wire increases in the sixth to eighth embodiments of the invention.

It is to be noted that the core wire may be energized concurrently at the time of starting the twisting procedure, or the core wire may be energized before or after starting the twisting procedure. The core wire may be energized to have a maximum temperature before or after the core wire reaches the predetermined turns of twist.

When the core wire may be energized to the maximum temperature before the core wire reaches the predetermined turns of twist, it becomes effective in preventing the possible disconnection of the core wire, and becomes appropriate to achieve a higher whole cross sectional reduction ratio (e.g., 94%-97.6%).

When the core wire may be energized to the maximum temperature after the core wire reaches the predetermined turns of twist, it becomes appropriate to achieve a lower whole cross sectional reduction ratio (e.g., 90% or more, but less than 94% exclusively). Whether the former or the latter procedure is selected may depend on the tensile rupture strength required for the core wire, the grinding capability or the residual angle left after bending the core wire in one direction or other.

The austenitic stainless steel wire employed to the core wire gradually increases the mechanical strength as the core wire is tightly wrought out, and the core wire attains a higher mechanical strength when the core wire is drawn until the whole cross sectional reduction ratio reaches 90%-97.6%.

By twisting the core wire as the cold working procedure, it becomes possible to render the texture more minutely so as to further increase the mechanical strength. Especially when the core wire is subjected to the twisting procedure with the whole cross sectional reduction ratio more than 94%, the twisting procedure develops a remarkable inequality of the hardness distribution between the outer layer and the inner layer of the core wire, thereby leading often to the possible disconnection of the core wire although the tensile rupture strength becomes higher.

In order to avoid the possible disconnection of the core wire, it becomes an effective measure to gradually heat the core wire until the core wire reaches the predetermined temperature with the increase of the twisting turns of the core wire. This makes it possible to remove the residual stresses which locally appear in accompany with the texture being minutely rendered as the twisting procedure advances, while at the same time, removing the residual stresses increasingly developed with the increase of the twisting turns of the core wire.

This also makes it possible to rectify the inequality of the hardness distribution between the outer layer and the inner layer of the core wire to an acceptable degree, and facilitating more to remove the residual stresses locally developed in the core wire.

As a consequence, it becomes possible to provide the core wire with a high tensile rupture strength, increased straightness and minimum residual angle left after bending the core wire in the bending experimentation test.

This also enables the manufacturer to produce the guide wire which is capable to maintain the quality stable by preventing the possible disconnection of the core wire when the core wire is twisted after wrought out in the drawing procedure.

Tables 4 and 5 show characteristics of the tensile rupture strength of the core wire 2 after the final heat treatment (low heat treatment at 385° C. for 30 minutes) in Tables 1, 2 and 3.

The core wire 2 has the distal end portion 21 ground to produce a ground portion at the distal end portion 21. The ground portion is pressed to form a plate structure rectangular in cross section which measures 0.094 mm in breadth and 0.030 mm in thickness. After placing the spring body 3 around the distal end portion 21 of the core wire 2, a synthetic layer is coated on the outer surface of the spring body 3 by means of an extruding procedure, a dipping procedure or a heat shrinkage tube with the use of thermoplastic synthetics (e.g., polyurethane or polyamide).

At the time of coating the synthetic layer on the spring body 3 at 180° C.-300° C. for ⅙-60 minutes, a certain amount of heat from a layer-forming machine or a shrinkage-tube heating machine (not shown) is used to the distal end portion 21 and the proximal end portion 22 of the core wire 2 in the low heat treatment. When the polyurethane is employed to the synthetic layer, the core wire is heated at 200° C. for 5 minutes in the low heat treatment.

Ninth, tenth and eleventh embodiments of the invention in Table 4 correspond to the first, second and sixth embodiments of the invention respectively. Twelfth and thirteenth embodiments of the invention in Table 5 correspond to the seventh and eighth embodiments of the invention respectively. In each of the embodiments of the invention, the core wire is pressed and subjected to the low heat treatment (200° C. for 5 minutes).

TABLE 4

| Procedure | Embodiment 9 | Embodiment 10 | Embodiment 11 |
|---|---|---|---|
| tensile rupture strength (kgf/mm$^2$) prior to pressing procedure | 259 | 280 | 290 |
| core: outer diameter (mm) | 0.150 | 0.150 | 0.150 |
| rectangular: width (mm) | 0.094 | 0.094 | 0.094 |
| thickness (mm) | 0.030 | 0.030 | 0.030 |

TABLE 4-continued

| Procedure | Embodiment 9 | Embodiment 10 | Embodiment 11 |
|---|---|---|---|
| low heat treatment (synthetics) temp. time | 200° C. for 5 min. | 200° C. for 5 min. | 200° C. for 5 min. |
| tensile rupture strength (kgf/mm2) | 262 | 283 | 293 |
| increase rated (%) | 1.2 | 1.1 | 1.0 |
| whole cross sectional reduction ratio (%) | 90 | 94 | 94.8 |

TABLE 5

| Procedure | Embodiment 12 | Embodiment 13 |
|---|---|---|
| tensile rupture strength (kgf/mm$^2$) prior to pressing procedure | 315 | 330 |
| core: outer diameter (mm) | 0.150 | 0.150 |
| rectangular: width (mm) | 0.094 | 0.094 |
| thickness (mm) | 0.030 | 0.030 |
| low heat treatment (synthetics) temp. time | 200° C. for 5 min. | 200° C. for 5 min. |
| tensile rupture strength (kgf/mm2) | 317 | 332 |
| increase rate (%) | 0.6 | 0.6 |
| whole cross sectional reduction ratio (%) | 96 | 97.6 |

As observed in Tables 4 and 5, the core wire shows the increase rate of the tensile rupture strength as 1.2% (the ninth embodiment of the invention), 1.1% (the tenth embodiment of the invention) and 1.0% (the eleventh embodiment of the invention) under the low heat treatment (e.g., 200° C. for 5 minutes) by using the heat at the time of coating the synthetic layer on the spring body 3 after pressing the core wire 2. The core wire exhibits the increase rate of the tensile rupture strength as 0.6% each in the twelfth and thirteenth embodiments of the invention.

When the distal end portion of the core wire is pressed to be rectangular in cross section, the tensile rupture strength of the pressed portion increases by 6.6 gf calculated in terms of a cross sectional area in the ninth, tenth and eleventh embodiments of the invention. In the twelfth and thirteenth embodiments of the invention, the tensile rupture strength of the pressed portion increases by approximately 4.4 gf.

Since the tensile rupture strength required for the head plug 5 and the core wire 2 is around 250 gf, and a connection between the head plug and the core wire 2 is a portion which is manipulated to be repeatedly bent upon navigating the core wire through the stenotic area of the coronary artery, the connection area requires a sufficient fatigue-resistant property against repetitive bending manipulations. Considering that the number of cyclic endurance is represented by stress endurance diagram (S-N diagram), even a small increase of the tensile rupture strength leads to a remarkable result of the number of cyclic endurance.

From the above point of view, the invention presents a technological idea convenient to improve the tensile rupture strength locally at the required place by making use of the heat upon forming the synthetic layer or contracting the shrinkage tube without using the thermal atmosphere from the heat due to the furnace.

It becomes possible to improve the tensile rupture strength by using the heat upon forming the synthetic layer 6 on the spring body 3. This is because the core wire 2 has the distal end portion 21 pressed to be rectangular in cross section (0.094 mm in breadth, 0.030 mm in thickness), and the concentrated stress developed on the pressed portion are equally dispersed. In addition, since the distal end portion 21 of the core wire 2 is hermetically sealed by the synthetic layer 6, the synthetic layer 6 contains the heat inside so as to render the heat reluctant to escape.

Moreover, the distal end portion 21 of the core wire 2 is thinned, and the pressed portion is exceedingly thinned so that the distal end portion 21 is very vulnerable to the thermal influence with a small heat capacity. The austenitic stainless steel wire is a material reluctant to be cooled soon with a low thermal conductivity.

The reason why the core wire is heated in the range of 180° C.-300° C., is to take into consideration the tensile strength characteristic of the austenitic stainless steel wire, the melting temperature of the synthetic layer, the thermal conductivity of the austenitic stainless steel wire and the thermal insulation due to the hermetic seal of the synthetic layer.

The reason why the core wire is heated for ⅙-60 minutes, is that if the heating time period is less than ⅙ minutes, it is difficult to provide a sufficient amount of the tensile rupture strength, and if the heating time period exceeds 60 minutes, it is not possible to expect a remarkable improvement of the tensile rupture strength. The heating time period contains a time taken for curing the synthetic layer, and a time capable to keep the core wire warm after forming the synthetic layer.

In Tables 4 and 5, the core wire 2 shows the tensile rupture strength as 260 kgf/mm$^2$ or more by implementing the low heat treatment after completing the grinding procedure (mechanical procedure) with the whole cross sectional reduction ratio as 90%-97.6%. The core wire exhibits the tensile rupture strength as 260 kgf/mm$^2$ or more with the stable quality of the product taken into consideration.

Additionally, the core wire 2 can show the tensile rupture strength as 300 kgf/mm$^2$ or more by implementing the low heat treatment after completing the mechanical procedure with the whole cross sectional reduction ratio as 96%-97.6%, thereby enabling the manufacturer to produce a guide wire with a higher tensile rupture strength.

In order to avoid cracks and nicks to develop on the distal end portion of the core wire upon pressing the distal end portion, it is preferable to set the tensile rupture strength to be 350 kgf/mm$^2$ or less, and more preferably 325 kgf/mm$^2$ or less.

Following are how the core wire changes the tensile rupture strength and the residual angle after twisting the core wire while heating the core wire by its electrical resistance depending on whether or not the core wire is heat treated.

Figure 10:
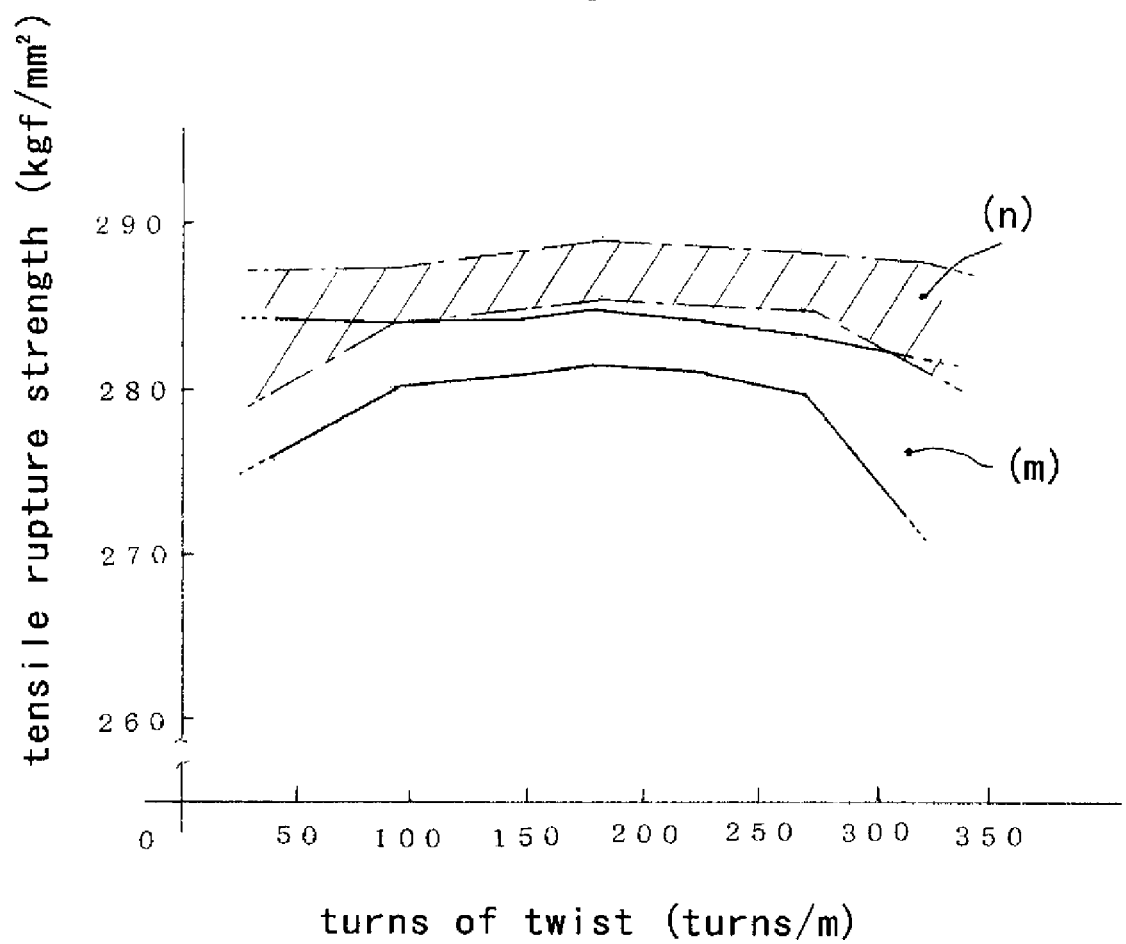
FIG. 10 is a graphical representation of a tensile strength characteristic showing a relationship between a tensile rupture strength and number of twisting turns under a heat treatment at low temperature.

FIG. 10 shows graphical representations as observed by designations (m), (n). The graphical representation (m) depicts how the tensile rupture strength changes depending on the twisting turns of the core wire under the condition that the core wire is energized to heat itself due to the electrical resistance. The graphical representation (n) depicts how the tensile rupture strength changes depending on the twisting turns of the core wire when subjected to the low heat treatment (450° C. for 120 minutes) after twisted under the condition that the core wire is energized to heat itself due to the electrical resistance.

Upon carrying out the above experimental tests, fifty specimens are adopted in each of the experimental tests with certain variations included.

Figure 11:
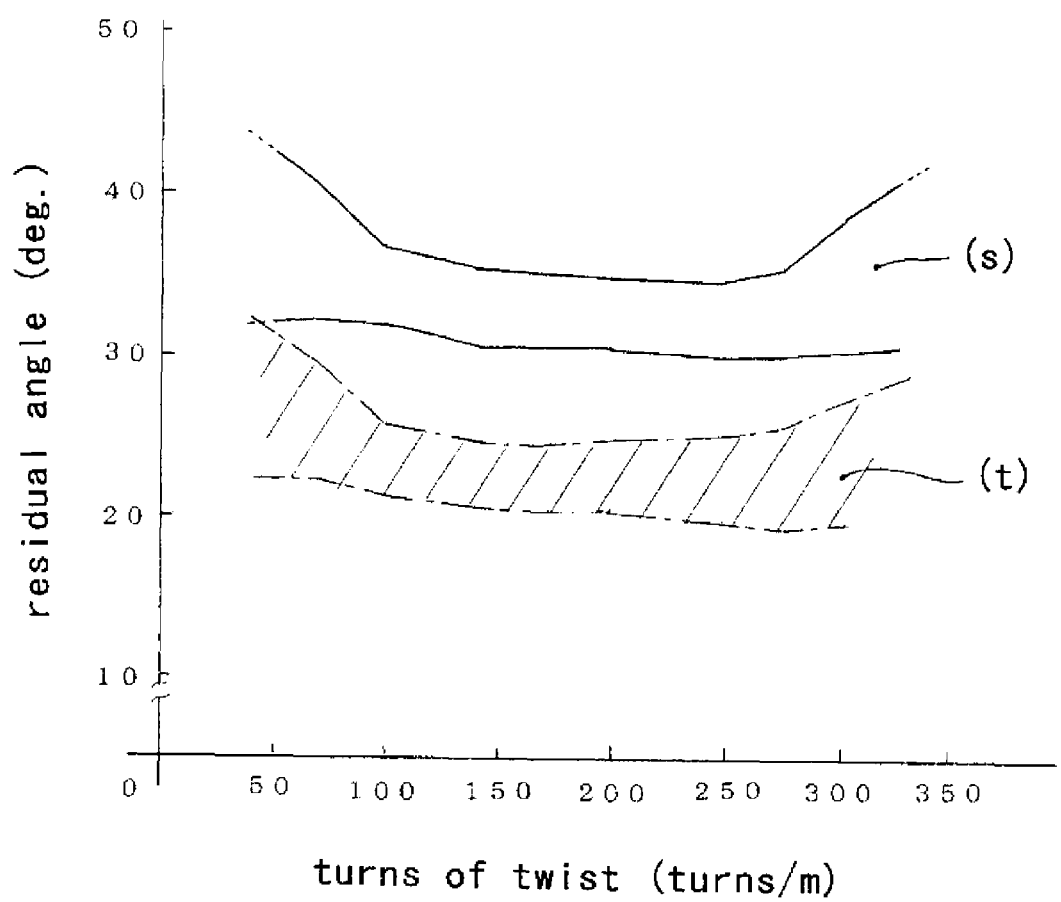
FIG. 11 is a graphical representation of a characteristic curve showing a relationship between a residual angle and number of twisting turns under a heat treatment at low temperature.

FIG. 11 shows graphical representations as observed by designations (s), (t). The graphical representation (s) depicts how the residual angle changes depending on the twisting turns of the core wire under the condition that the core wire is energized to heat itself due to the electrical resistance. The graphical representation (t) depicts how the residual angle changes depending on the twisting turns of the core wire when subjected to the low heat treatment (450° C. for 120 minutes) after twisted under the condition that the core wire is energized to heat itself due to the electrical resistance.

It is to be noted that the residual angle develops at the time of carrying out the bending experimentation test in which the core wire 2 is angularly bent around a circular bar (15 mm in diameter) by 180 degrees to form a bent portion with the core wire 2 loaded by a tensile weight (500 grams) for 20 seconds. Thereafter, the core wire 2 is unloaded to measure how much angle the bent portion forms as the residual angle against the axial direction of the core wire 2.

Namely, the residual angle is an angular gradient developed against the axial direction when the core wire 2 is plastically deformed at the bending experimentation test.

As observed in FIG. 10, the core wire 2 shows small fluctuations of the tensile rupture strength with the turns of twist remained in the range of 100-275 turns per meter, and the core wire 2 exhibits an increase of the fluctuations outside the range prescribed above. As observed in FIG. 11, the core wire 2 shows small fluctuations of the residual angle with the turns of twist remained in the range of 100-275 turns per meter, and the core wire 2 exhibits an increase of the fluctuations outside the range prescribed above.

This is because when the turns of twist comes to less than 100 turns per meter, the core wire 2 remains unhomogeneous texture inside along the axial direction due to the insufficient turns of twist, and when the turns of twist exceeds 275-325 turns per meter, the core wire 2 develops Lders line (stretcher line) as an excessive turns of twist, thereby forming the angular gradient (approx. 45 degrees) against the axial direction so as to disperse the unhomogeneous texture in the core wire 2. In the concept of the invention, the twisting procedure has no meaning to implement the excessive turns of twist as represented by Lders line.

The core wire 2 shows the least residual angle when the turns of twist comes to 100-200 turns per meter. It is preferable to set the turns of twist to be 120-180 turns per meter, more preferably 10%-30% of the preferable turns of twist, and it is most preferable to twist the core wire reversely by 20% of the normal turns of twist. More specifically, it is preferable to reversely twist the core wire by 12-36 turns per meter, more preferably 24 turns per meter after normally twisting the core wire by 120 turns per meter.

By adding the reverse twist to the core wire, it becomes possible to release the stresses remained in the core wire when normally twisted. This effectuates the low heat treatment to provide the core wire 2 with an improved straightness (linearity).

Figure 12:
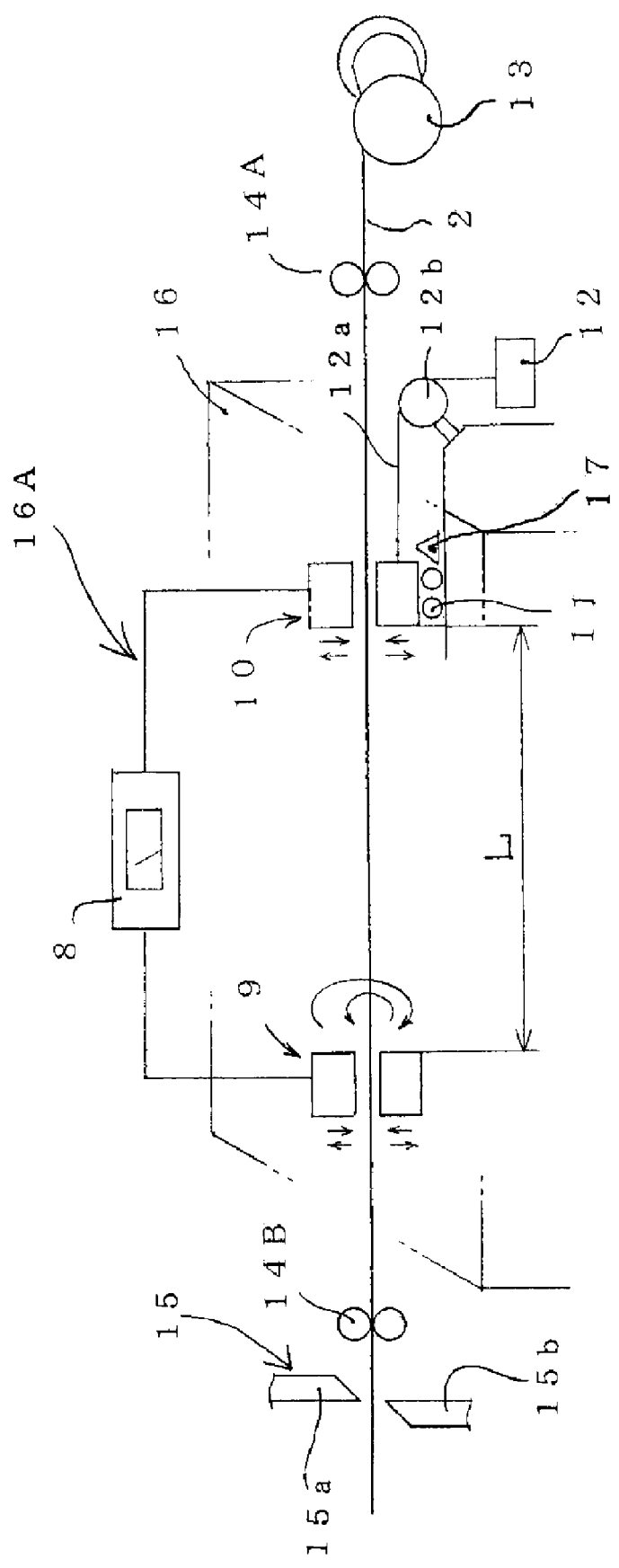
FIG. 12 is a schematic view of a manufacturing device in which the core wire is twisted under the low heat treatment due to its electrical resistance.

FIG. 12 shows a manufacturing device 16A which is installed to implement the twisting procedure and the heating procedure due to electrical resistance of the core wire 2.

A bobbin 13 releases the core wire 2 through guide rollers 14A and feed rollers 14B toward an insulation casing 16 which is installed to keep the core wire 2 warm. The core wire 2 is fixed by a rotatable chuck 9 and a slidable chuck 10, the latter of which is to slide along the axial direction of the core wire 2. The core wire 2 is to be energized to be heated by a power generator 8.

A wire line 12a is provided to connect the tensile weight 12 to the slidable chuck 10 through a pulley 12b so as to give a tension to the core wire 2 along its axial direction. The rotatable chuck 9 twists the core wire 2 by certain turns of twist in the normal direction with the core wire 2 fixedly secured by the slidable chuck 10. Thereafter, it becomes preferable that the core wire 2 is reversely twisted by certain turns of twist.

More specifically, when the core wire 2 measures 0.340 mm in diameter with a lengthwise span L set between the rotatable chuck 9 and the slidable chuck 10 as 4000 mm, after twisting the core wire 2 by 400-800 turns in one direction with the weight 12 applied to the core wire 2, the core wire 2 is preferably twisted 80-160 turns (20% of 400-800 times) in another direction.

These twisting procedures are implemented under the low heat treatment by energizing the core wire 2 to generate the heat due to the electrical resistance. After the twisting procedure held under the low heat treatment, the core wire 2 is released from the constraint of the rotatable chuck 9 and the slidable chuck 10, and sent leftward with the help of the guide rollers 14A and the feed rollers 14B. At a scissors gate 15, a pair of cutter blades 15a, 15b is employed to sever the core wire 2 (wrought-out wire) at the predetermined length as a cutting procedure. By repeating the cutting procedure thereafter, it is possible to consecutively produce the core wire 2 superior in straightness.

It is to be noted that the core wire 2 may be energized to progressively increase the generation of heat with the increase of the turns of twist in the above procedures.

During the process in which the manufacturing device 16A is used, the core wire 2 is pulled out of the bobbin 13 to be placed within the insulation casing 16 (pulling step). The core wire 2 is fixed to the rotatable chuck 9 and the slidable chuck 10 (fixing step), and the slidable chuck 10 is released from the constraint of a stopper 17 to slide along the axial direction, while at the same time, imposing the weight 12 on the core wire 2 in the tensile direction (loading step).

Then, the core wire 2 is energized by the power generator 8 within the insulation casing 16 provided to keep the core wire 2 warm at a certain temperature (energizing step). The core wire 2 is twisted by certain turns of twist in one direction with the use of the rotatable chuck 9 while being energized to be heated by its electrical resistance (twisting step).

In the twisting step, the core wire 2 may be energized to progressively increase the generation of heat with the increase of the turns of twist. After twisting the core wire 2, the stopper 17 is applied to the slidable chuck 10 so as to prevent the chuck 10 from sliding toward the weight 12 through the wire line 12a when the slidable chuck 10 releases the core wire 2 (applying step).

The core wire 2 is released from the constraint of the rotatable chuck 9 and the slidable chuck 10 (releasing step), and pulled toward the scissors gate 15 through the guide rollers 14A and the feed rollers 14B (forwarding step). After pulling out the core wire 2, the core wire 2 is severed at the predetermined length by the cutter blades 15a, 15b (severing step). These processes enables the manufacturer to consecutively produce the core wire 2 twisted under the low heat treatment due to the electrical resistance.

It is to be note that the core wire may be severed beforehand at the predetermined length, and then the core wire 2 is twisted in the same manner as described above.

During the above processes, the core wire 2 is subjected to the low heat treatment due to the electrical resistance at 380° C.-495° C. with the applied time period as ½-60 minutes (e.g., 450° C. for 5 minutes). Through the line wire 12a, the weight 12 applies the tensile load to the core wire 2 preferably by 5%-30% (more preferably 10%-25%, most preferably 20%) of the tensile rupture strength represented after the final drawing procedure.

More specifically, since the core wire 2 exhibits its diameter as 0.228 mm with the tensile rupture strength as 302 kgf/mm² after the final drawing procedure, but before the twisting procedure, the core wire 2 is estimated at its tensile rupture strength as 12.32 kgf {(0.228×302×π)/4}, and the weight 12 is calculated to be 2.46 kgf (12.32×0.2) in the most preferable case.

When the weight 12 is outside the range of 5%-30% of the tensile rupture strength, the lightweight core wire would deform wavy, and the heavy core wire would lead to disconnection, resulting to the failure to achieve the core wire 2 superior in straightness and productivity.

Before implementing the twisting procedure, it is important to adjust the load of the weight 12 depending on the tensile rupture force based on the tensile rupture strength of the core wire 2. The tensile rupture force means an upper limit of the load when the core wire surrenders to collapse upon applying a tensile force to the core wire 2.

As mentioned above, the core wire 2 is heated at 380° C.-495° C. for 21-60 minutes in the low heat treatment, and the core wire 2 is twisted by 100-275 turns/m (preferably 100-200 turns/m, more preferably 120-180 turns/m). Preferably, the core wire 2 is reversely twisted by 10%-30% of the normal twisting procedure implemented prior to the reverse twisting procedure. The weight 12 preferably has the tensile load, the magnitude of which is 5%-30% (most preferably 20%) of the tensile rupture force.

The above conditions satisfy the requirements for the guide wire to meet as the characteristics regarding the tensile rupture strength, the straightness (linearity) and the torque-transmission.

FIG. 13 shows the characteristic of the tensile rupture strength of the austenitic stainless steel wire (SUS304, 1.5 mm in diameter) treated with the solid solution procedure in the third and sixth embodiments of the invention. The austenitic stainless steel wire is drawn to be 0.340 mm in diameter with the cross sectional reduction ratio as 94.8%. The austenitic stainless steel wire is ground as the core wire 2 to be 0.150 mm in diameter, and heated for 30 minutes in each temperature in FIG. 13.

As observed in FIG. 13, the tensile rupture strength starts to rise at 180° C., and reaches a maximum around at 450° C., continuing to improve the tensile rupture strength until risen up to 495° C.

When the temperature exceeds 500° C.-520° C., the temperature abruptly deteriorates the characteristic of the tensile rupture strength in comparison with the core wire treated at the normal temperature (20° C.).

Reasons why the tensile rupture strength deteriorates are as follows:

When the austenitic stainless steel wire is heated to the temperature of 500° C.-850° C., it requires an energy to precipitate the carbon particles and mobilize chromium within the austenitic stainless steel wire (susceptive phenomenon). Especially, for the austenitic stainless steel wire (SUS304) which contains carbon in less than 0.08%, it begins to be susceptible to the thermal influence at 700° C. so as to exceedingly reduce the tensile rupture strength in 4-5 minutes.

Under the condition that the distal end portion 21 of the core wire 2 is susceptible to the thermal influence, the circular end tip 23 (FIG. 5) of the distal end portion 21 approximately measures 0.060 mm-0.150 mm in diameter which is produced by grinding the austenitic stainless steel wire (approx. 0.340 mm in diameter) with the use of a centerless grinder or the equivalents.

As observed by a graphical representation in FIG. 13, the tensile rupture stress 250 kgf/mm² at the normal temperature rises by approximately 6.4% to 266 kgf/mm² by heating the austenitic stainless steel wire to 180° C.

At the temperature of 450° C., the tensile rupture stress rises by approximately 16% to 290 kgf/mm² (maximum value). By converting the tensile rupture stress to the tensile strength with the use of the cross sectional area, the distal end portion 21 of the core wire increases its tensile strength by 113 gf from 706 gf to 819 gf.

At the temperature of 495° C., the tensile rupture stress rises to 260 kgf/mm², i.e., about 4% increase compared to the tensile rupture stress at the normal temperature.

When the temperature exceeds 500° C.-520° C., the susceptive phenomenon appears to reduce the tensile rupture strength, so that the tensile rupture strength comes to 210 kgf/mm², meaning that the tensile rupture force significantly decreases from 819 gf to 593 gf so as to break the distal end portion 21 at an exceedingly low tensile force.

It is to be noted that the tensile rupture stress observed at 250 kfg/mm² (room temperature) in FIG. 13 varies depending on the cross sectional reduction ratio and conditions of the grinding procedure. The characteristic of the tensile rupture strength changes depending on the temperature in the same manner as mentioned above.

Unless the welding member 4 (eutectic alloy) is used with the tensile strength characteristic taken into consideration, the core wire 2 deteriorates its tensile strength due to the melting heat generated from the eutectic alloy when the core wire 2 and the spring body 3 are welded despite the core wire 2 is work hardened to increase the tensile strength during the drawing process. The reduced tensile strength may fall the head plug 5 off the core wire 2 due to the bending fatigue while navigating the guide wire 1 through the vasculature.

With the above characteristic of the tensile rupture strength taken into consideration, it is preferable to heat the core wire 2 at 180° C.-495° C. in the low heat treatment, and the low heat treatment at 450° C. after the final drawing procedure is appropriate as observed in Tables 1-3. The characteristic of the tensile rupture strength becomes remarkable by the low heat treatment at 385° C. when making use of the heat upon forming the synthetic layer 6 from the fluoride-based resin (e.g., PTFE). So does it by the low heat treatment at 200° C. when making use of the heat upon forming the synthetic layer 6 on the outer surface of the spring body 3 after pressing the core wire 2 as observed in Tables 4, 5.

Observing the characteristic of the tensile rupture strength attained from the austenitic stainless steel wire tightly drawn at the higher cross sectional reduction ratio, the austenitic stainless steel wire is appropriately processed at the low heat treatment after tightly drawn, while at the same time, making use of the heat upon forming the synthetic layer 6 within a certain range of temperature. This make it possible to significantly improve the characteristic of the tensile rupture strength with the help of the hermetic seal effect (warmth keeping effect), the thermal conductivity, the structure and the material involving the core wire 2.

Following are procedures depicting how to draw the core wire in order to improve the characteristic of the tensile rupture strength in the sixth embodiment of the invention.

By only drawing the core wire 2 with the whole cross sectional reduction ratio as 94.8%, it is not sufficient to impart the high tensile strength to the core wire 2 with the use of the austenitic stainless steel wire (solid solution) as observed in FIG. 13.

By way of example, the primary drawing procedure is implemented by consecutively drawing the austenitic stainless steel wire (1.5 mm in diameter) through tens of arranged dices (10-20), each of which is capable of drawing with the whole cross sectional reduction ratio as 4%-20%.

During the drawing process, the core wire is drawn so that its diameter reduces to 0.5 mm with the whole cross sectional reduction ratio as 88.9%.

After heat treating the core wire at 400° C.-450° C. (low temperature) for 20-120 minutes (e.g., 420° C. for 75 minutes), the secondary drawing procedure is implemented by consecutively drawing the core wire (0.340 mm in diameter) through the several dices (5-8) with the whole cross sectional reduction ratio as 53.8%. The latter procedure is repeated depending on the situation until the whole cross sectional reduction ratio comes to 94.8% with the desired tensile strength achieved in the distal end portion 21 of the core wire 2.

In this instance, it is preferable that the whole cross sectional reduction ratio in the primary drawing procedure is greater than the whole cross sectional reduction ratio in the secondary drawing procedure upon providing the high tensile strength with the size-reduced intermetallic grains in the core wire 2 and improving the productivity from an economic point of view.

It is to be noted that the dices are preferably made of the natural diamond rather than an alloyed metal because the diamond is superior in frictional resistance and appropriate when drawing the high strength wire as observed above.

In the final drawing procedure, it is preferable to arrange the several dices (5-8) with the last dice capable to give the core wire the value of 4%-13% as the least one among the whole cross sectional reduction ratio 4%-20%, thus making it possible to prevent the disconnection so as to produce the core wire superior in productivity and stable in quality.

The austenitic stainless steel wire of the present invention has chemical composition as follows:

C: less than 0.15% by weight, Si: less than 1.0% by weight, Mn: less than 2.0% by weight, Ni: 6%-16% by weight, Cr: 16%-20% by weight, P: less than 0.045%, S: less than 0.030%, Mo: less than 3.0%, balance: iron and impure substances unavoidably contained.

Without using a high silicic stainless steel (Si: 3.0%-5.0% by weight), it is possible to provide the core wire 2 with the high tensile strength by means of the austenitic stainless steel wire (represented by SUS304, SUS316).

Apart from the austenitic stainless steel wire treated with the solid solution to improve the tensile rupture strength, following are ways to improve the tensile rupture strength from other perspective.

From the graphical representation in FIG. 13, it is effective in improving the tensile rupture strength under the low heat treatment at 180° C.-495° C. By using the eutectic alloy to the welding members 41-43 and the head plug 5 in order to have the melting temperature between 180° C.-495° C., it becomes possible to ameliorate the tensile rupture strength.

More specifically, the welding members 41, 42 are shaped into a ring-shaped configuration, and placed between the core wire 2 and the spring body 3 to partly weld therebetween. Each of the welding members 41, 42 measures 0.228 mm-0.340 mm in diameter and 0.3 mm-1.5 mm in thickness (or width).

The welding member 43 is formed into a disc-shaped configuration, and welds the radiotransparent coil 32 to the core wire 2 (0.200 mm-0.340 mm in diameter). The welding member 43 measures 0.228 mm-0.340 mm in diameter and 0.3 mm-3.0 mm in thickness (width). The welding member 43 may be formed into a cone-shaped configuration which is tapered off as approaching the distal end portion 21 of the core wire 2. It is to be noted that partly welding with the use of the welding member 4 means to weld the spring body 3 to the core wire 2 through the welding members 41-43.

The eutectic alloy means a special alloyed metal, components of which can be adjusted to gain a lowest melting temperature.

As a gold-tin based alloy, it contains 80% gold by weight and 20% tin by weight to have the melting temperature of 280° C. As a silver-tin based alloy, it contains 3.5% silver by weight and 96.5% tin by weight to have the melting temperature of 221° C. As a gold-germanium based alloy, it contains 88% gold by weight and 12% germanium by weight to have the melting temperature of 356° C. As gold-tin-indium based alloys, they are represented to have the melting temperature of 450° C.-472° C. as shown in Table 6.

TABLE 6

| No. | Eutectic Alloy (%) (by weight) | | | Melting Temp. |
|---|---|---|---|---|
| A-1 | gold (80%) | tin (20%) | | 280° C. |
| A-2 | gold (10%) | tin (90%) | | 217° C. |
| A-3 | gold (88%) | germanium (12%) | | 356° C. |
| A-4 | gold (73.3%) | indium (26.7%) | | 451° C. |
| B-1 | silver (3.5%) | tin (96.5%) | | 221° C. |
| B-2 | silver (40%) | tin (30%) | indium (30%) | 450° C. |
| B-3 | silver (40%) | tin (40%) | indium (10%) copper (10%) | 458° C. |
| B-4 | silver (45%) | tin (45%) | indium (10%) | 472° C. |

Figure 15:
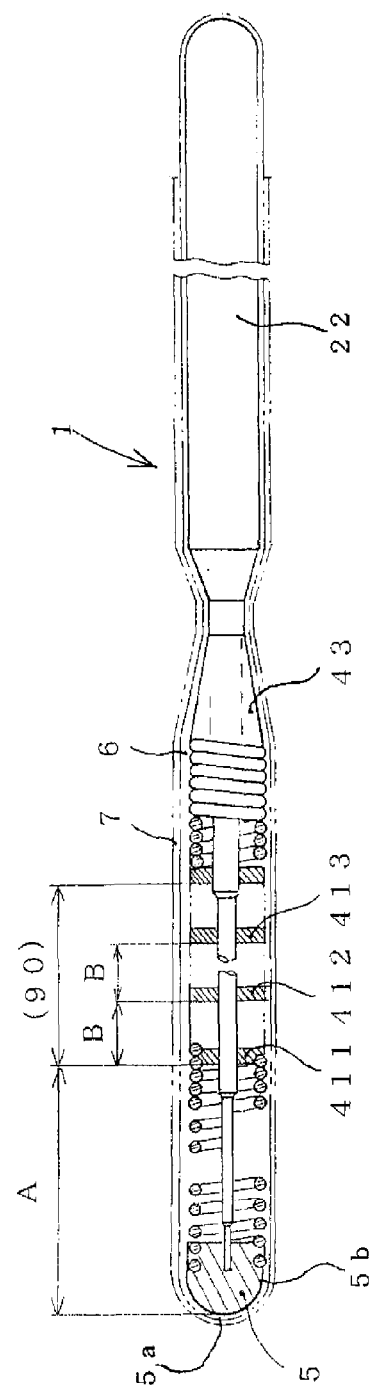
FIG. 15 is a plan view of a medical guide wire but partly sectioned according to other embodiment of the invention.
Figure 16:
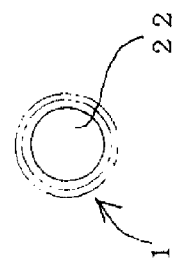
FIG. 16 is a right side elevational view of the medical guide wire.

As shown in FIGS. 15, 16, ten middle welding sections 411-420 are provided between the core wire 2 and the spring body 3 with the use of the welding member 4 as other embodiment of the invention although the middle welding sections 414-420 are not shown.

These middle welding sections 411-420 are arranged longitudinally at regular intervals (B: 10 mm) by a predetermined length (e.g., 90 mm) proximally from a distance A (e.g., 50 mm) off the distal extremity of the head plug 5.

This enables the manufacturer to implement the low heat treatment along the extension (90 mm in length) so as to help ameliorate the tensile rupture strength of the core wire 2.

It becomes possible to heat a part of the core wire 2 to increase the tensile rupture strength of a needed portion without setting the furnace to heat an entire region of the core wire 2.

With the middle welding sections 411-420 arranged at regular intervals, when therapeutically treating a stenotic lesion developed in the blood vessel, it becomes possible to measure a lengthwise dimension of the stenotic lesion under the fluoroscopy.

That the middle welding sections 411-420 are dimensionally located as above, is that the middle welding sections 411-420 would correspond to the stenotic lesion often found in the coronary artery when navigating the guide wire 1 through the coronary artery.

By using the eutectic alloy to the head plug 5, it becomes possible to increase the tensile rupture strength of the core wire 2 at the welded portion between the head plug 5 and the core wire 2, thereby providing the welded portion with an improved fatigue-resistant property against repetitive bending manipulations within the stenotic lesion.

It is to be noted that the middle welding sections 411-420 (including the head plug 5) are welded after heat treating the ground portion of the distal end portion 21 at low temperature (385° C.) for 30 minutes, and securing the spring body 3 to the distal end portion 21. Thereafter, the synthetic layer 6 is coated on the outer surface of the spring body 3.

By using the improved tensile rupture strength of the core wire 2, it becomes possible to diametrically thin the core wire 2 of the guide wire 1.

By way of example, the improved tensile rupture strength makes it possible to thin the proximal portion of the guide wire 1 from 0.355 mm to 0.254 mm (0.014 inches to 0.010 inches).

By further using the heat upon forming the synthetic layer 6, and the heat remained within the hermetic seal portion upon forming the synthetic layer 6, it becomes possible to further ameliorate the tensile rupture strength of the distal end portion 21, thereby thinning the core wire 2 to be 0.228 mm (0.009 inches) in diameter.

Upon implementing the therapeutical treatment against the vascular stenosis, the guide wire 1 is inserted into a microcatheter (not shown), and the guide wire 1 inserted into the microcatheter is further inserted into a guiding catheter (not shown) together with the microcatheter.

In accompany with the guide wire 1 being thinned, the guiding catheter is also thinned from 7F-8F (2.3 mm-2.7 mm in inner diameter) to 5F-6F (1.59 mm-2.00 mm in inner diameter), while at the same time, thinning the guiding catheter to be 0.28 m-0.90 mm in inner diameter. This makes it possible to render the guide wire 1 minimally intrusive so as to lessen the burden which the patient suffers from when therapeutically treated.

Since when inserting the microcatheter and the guide wire to an entry of the stenotic lesion through the coronary artery, the guide wire develops a reactionary force upon inserting the guide wire to the coronary artery, it becomes possible to provide a forward-propelling force with the guide wire by supporting the guide wire with the microcatheter.

The microcatheter may be made of multi-layered synthetic tubes, or multi-layered synthetic tubes which are strengthened by braided thin wires. Otherwise, the microcatheter may be a wire-stranded tube body made by stranding a plurality of wires in a helical fashion with a cone-shaped metal tip provided on a distal end thereof. This makes wire-stranded tube body perforative against an obstructed area within the stenotic lesion.

Since it becomes possible to diametrically thin the proximal portion 22 of the guide wire 1 from 0.355 mm to 0.254 mm (0.014 inches to 0.010 inches), and further to 0.228 mm (0.009 inches), the guide wire is inserted into a balloon catheter (not shown), and the guide wire 1 inserted into the balloon catheter is further inserted into a guiding catheter (not shown) together with the balloon catheter upon implementing the therapeutical treatment against the vascular stenosis.

In accompany with the guide wire 1 being thinned, the guiding catheter being also thinned from 7F-8F (2.3 mm-2.7 mm in inner diameter) to 5F-6F (1.59 mm-2.0 mm in inner diameter), while at the same time, thinning the balloon catheter to be 0.28 m-0.90 mm in inner diameter. This makes it possible to render the guide wire 1 minimally intrusive so as to lessen the burden which the patient suffers from when therapeutically treated.

Two sets of catheters in which the guide wire 1 is combined with the balloon catheter are prepared. Each set of the catheters is placed into the guiding catheter to implement the kissing manipulation in which balloons are concurrently inflated at a bifurcated portion of the vascular stenosis.

As apparent from the foregoing description, the invention is made by considering the fact that the austenitic stainless steel wire increases its characteristic of the tensile rupture strength depending on the temperature after the stainless steel wire is tightly drawn near its limit. Upon manufacturing the core wire, the drawing procedure and the low heat treatment are alternately repeated. The twisting procedure is implemented under the low heat treatment to provide the core wire with a superior straightness and rotation-following capability. The low heat treatment is held within a certain range of temperature after the core wire is ground as a mechanical procedure. The core wire comes to increase the tensile rupture strength cumulatively each time when the procedures are implemented, thereby making it possible to produce a medical guide wire with an improved tensile rupture strength.

Additionally, the proximal end portion 22 of the core wire 2 is treated by the heat upon forming (drying and sintering) the synthetic layer with a relatively high temperature. The distal end portion 21 of the core wire 2 is treated by the heat upon forming the synthetic layer on the outer surface of the spring body 3 after grinding and pressing the distal end portion 21 of the core wire 2.

By considering how the tensile rupture strength increases depending on the temperature upon drawing and heat treating the core wire, it becomes possible to increase the tensile rupture strength of a part or entirety of the core wire. This enables the manufacturer to increase the mechanical strength of the distal end portion of the medical guide wire with a stable quality consistently maintained although the distal end portion of the medical guide wire is thinned.

While several illustrative embodiments of the invention have been shown and described, numerous variations and alternate embodiments will occur to those skilled in the art. Such variations and alternate embodiments are contemplated, and can be made without departing from the spirit and scope of the invention as defined in the appended claims.

What is claimed is:

1. In a medical guide wire having a core wire formed of a flexible elongate member, a helical spring body inserted to a distal end portion of said core wire to be placed around said core wire, and a head plug provided at distal end tips of both said core wire and said helical spring body by means of a welding member, and a synthetic layer coated at least on an outer surface of a proximal portion of said core wire;
   said core wire made of austenitic stainless steel wire treated with a solid solution procedure, and drawn at a wire-drawing procedure and then heat treated at low temperature of 400° C.-495° C.;
   a final wire-drawing procedure defined after repeating at least more than a single set of procedures with a combination of said wire-drawing procedure and said heat-treating procedure as the single set;
   said core wire being rendered with a whole cross sectional reduction ratio as 90%-97.6% until said core wire is subjected to said final wire-drawing procedure;
   said core wire having 8% or more as a total increase rate of a tensile rupture strength attained due to said heat treatment procedure until said core wire is subjected to said final wire-drawing procedure;
   said core wire being subjected to predetermined turns of twist at low temperature of 380° C.-495° C. due to an electrical resistance caused by energizing said core wire after finishing said final wire-drawing procedure;
   said core wire being heat treated at low temperature of 340° C.-420° C. with the use of a heat generated when said synthetic layer is coated on said outer surface of said core wire after treating said distal end portion of said core wire with a mechanical procedure including grinding or pressing procedure;
   said core wire having 2% or more as a total increase rate of a tensile rupture strength attained each time when said core wire is subjected to said heat treatment procedure after said core wire is subjected to said final wire-drawing procedure; and
   said core wire having 10% or more as a total increase rate of a tensile rupture strength attained each time when said core wire is subjected to said heat treatment procedure.

2. The medical guide wire according to claim 1, wherein among said predetermined turns of twist, to which said core wire is subjected at low temperature of 380° C.-495° C. due to said electrical resistance caused by energizing said core wire, said predetermined turns of twisting procedure comprising a procedure in which said core wire is subjected to heat treatment, a temperature of which progressively increases with an increase of said turns of twist by said electrical resistance caused by energizing said core wire at low temperature of 380° C.-495° C. as a maximum temperature.

3. The medical guide wire according to claim 1 or 2, wherein a heat treatment procedure at low temperature is provided to heat treat said core wire at 400° C.-495° C. after treating said distal end portion of said core wire with said mechanical procedure, but before coating said synthetic layer on said core wire,
   said tensile rupture strength being increased compared to the tensile rupture strength after said mechanical procedure is implemented, said core wire having 11.5% or more as a total increase rate of the tensile rupture strength attained each time when said core wire is subjected to said heat treatment procedure.

4. The medical guide wire according to claim 1, wherein said welding member is formed by a eutectic alloy having a melting point of 180° C.-495° C.

5. An assembly of a microcatheter and a guiding catheter combined with said medical guide wire according to claim 1, wherein an outer diameter of said medical guide wire measures 0.228 mm-0.254 mm (0.009 inches-0.010 inches) which is inserted into said microcatheter, an inner diameter of which measures 0.28 mm-0.90 mm, and said medical guide wire inserted into said microcatheter is further inserted into said guiding catheter, an inner diameter of which ranges 1.59 mm to 2.00 mm.

6. An assembly of a balloon catheter and a guiding catheter combined with said medical guide wire according to claim 1, wherein an outer diameter of said medical guide wire measures 0.228 mm-0.254 mm (0.009 inches-0.010 inches) which is inserted into said balloon catheter, an inner diameter of which measures 0.28 mm-0.90 mm, and said medical guide wire inserted into said balloon catheter is further inserted into said guiding catheter, an inner diameter of which ranges 1.59 mm to 2.00 mm.

7. In a medical guide wire having a core wire formed of a flexible elongate member, a helical spring body inserted to a distal end portion of said core wire to be placed around said core wire, and a head plug provided at distal end tips both said core wire and said helical spring body by means of a welding member, and a synthetic layer coated at least on an outer surface of said helical spring body;
   said distal end portion of said core wire being ground, so that a ground portion of said core wire is heat treated at low temperature and said ground portion is pressed;
   at least a pressed portion of said core wire being heat treated at low temperature of 180° C.-300° C. due to a heat generated when coating said synthetic layer on said helical spring body; and
   a tensile rupture strength of said ground portion or said pressed portion of said core wire being increased compared to the tensile rupture strength which said distal end portion of said core wire has before being heat treated at low temperature of 180° C.-300° C. when coating said synthetic layer on said helical spring body.

8. In a method of making a medical guide wire having a core wire formed of a flexible elongate member, a helical spring body inserted to a distal end portion of said core wire to be placed around said core wire, and a head plug provided at distal end tips of both said core wire and said helical spring body by means of a welding member;
   said core wire made of austenitic stainless steel wire treated with a solid solution procedure, and drawn at a wire-drawing procedure and then heat treated at low temperature of 400° C.-495° C. for 10-180 minutes;
   a final wire-drawing procedure defined after repeating at least more than a single set of procedures with a combination of said wire-drawing procedure and said heat-treating procedure as the single set;
   said core wire being rendered with a whole cross sectional reduction ratio as 90%-97.6% until said core wire is subjected to said final wire-drawing procedure;
   twisting one end of said core wire around its axis by 100-275 turns per meter with the other end loaded by a tensile weight, a magnitude of which is 5%-30% of a tensile rupture strength before said core wire is twisted under the condition that said core wire is heat treated at low temperature of 380° C.-495° C. for 0.5-60 minutes due to an electrical resistance caused by energizing said core wire, said distal end portion of said core wire being ground or pressed after ground;

inserting said helical spring body to said distal end portion of said core wire to place said helical spring body around said distal end portion of said core wire;

partly securing said core wire and said helical spring body together by means of said welding member; and forming said head plug by welding said distal end tips of both said core wire and said helical spring body by means of said welding member.

9. The method of making a medical guide wire according to claim 8, wherein said core wire is further heat treated at low temperature of 400° C.-495° C. for 10-180 minutes after said one end of said core wire is twisted, but before said distal end portion of said core wire is ground or pressed after ground.

10. The method of making a medical guide wire according to claim 8, wherein a synthetic layer is coated at least on an outer surface of said helical spring body after said distal end portion of said core wire is ground or pressed after ground, and then at least a ground portion or a pressed portion of said distal end portion of said core wire is heat treated at low temperature of 340° C.-420° C. for 10-180 minutes before inserting said helical spring body to said distal end portion of said core wire.

11. The method of making a medical guide wire according to claim 8, wherein among said predetermined turns of twist, to which said core wire is subjected at low temperature of 380° C.-495° C. for 0.5-60 minutes due to said electrical resistance caused by energizing said core wire, said predetermined turns of twist comprising a first twisting procedure in which one end of said core wire is twisted around its axis by 100-275 turns per meter after said final wire-drawing procedure with the other end loaded by a tensile weight, a magnitude of which is 5%-30% of a tensile rupture strength before said core wire is twisted, and a second twisting procedure in which said core wire is subjected to heat, a temperature of which progressively increases with an increase of said turns of twist by said electrical resistance caused by energizing said core wire at low temperature of 380° C.-495° C. as a maximum temperature.

* * * * *